(12) United States Patent
Kondou

(10) Patent No.: US 8,376,951 B2
(45) Date of Patent: Feb. 19, 2013

(54) ULTRASONIC DIAGNOSTIC APPARATUS AND METHOD FOR DISPLAYING PROBE OPERATION GUIDE

(75) Inventor: Masanao Kondou, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/054,145

(22) PCT Filed: Jun. 24, 2009

(86) PCT No.: PCT/JP2009/061439
§ 371 (c)(1),
(2), (4) Date: Jan. 14, 2011

(87) PCT Pub. No.: WO2010/007860
PCT Pub. Date: Jan. 21, 2010

(65) Prior Publication Data
US 2011/0125020 A1 May 26, 2011

(30) Foreign Application Priority Data

Jul. 15, 2008 (JP) ................................. 2008-183808

(51) Int. Cl.
*A61B 8/14* (2006.01)
(52) U.S. Cl. .......................... 600/462; 600/437; 600/459
(58) Field of Classification Search ........... 600/437–469
See application file for complete search history.

(56) References Cited

U.S. PATENT DOCUMENTS

| 7,488,287 | B2 * | 2/2009 | Kawashima | 600/443 |
| 7,775,977 | B2 * | 8/2010 | Kawashima et al. | 600/437 |
| 8,023,712 | B2 * | 9/2011 | Ikuma et al. | 382/131 |
| 2004/0249287 | A1 * | 12/2004 | Kawashima et al. | 600/462 |
| 2005/0228275 | A1 * | 10/2005 | Kawashima | 600/437 |
| 2005/0256402 | A1 * | 11/2005 | Kawashima et al. | 600/437 |
| 2006/0079772 | A1 * | 4/2006 | Ichikawa et al. | 600/437 |
| 2007/0239009 | A1 * | 10/2007 | Kawashima et al. | 600/437 |
| 2008/0004529 | A1 * | 1/2008 | Kawashima et al. | 600/443 |
| 2008/0281189 | A1 * | 11/2008 | Komuro et al. | 600/424 |
| 2009/0175518 | A1 * | 7/2009 | Ikuma et al. | 382/128 |
| 2010/0208963 | A1 * | 8/2010 | Kruecker et al. | 382/131 |

FOREIGN PATENT DOCUMENTS

| JP | 2005-111143 | 4/2005 |
| JP | 2005-118161 | 5/2005 |
| JP | 2006-167267 | 6/2006 |
| WO | WO 2004/098414 A1 | 11/2004 |
| WO | WO 2006/059668 A1 | 6/2006 |
| WO | WO 2006/064676 A1 | 6/2006 |

* cited by examiner

*Primary Examiner* — Sanjay Cattungal
(74) *Attorney, Agent, or Firm* — Antonelli, Terry, Stout & Kraus, LLP.

(57) ABSTRACT

An ultrasonic diagnostic apparatus according to the present invention including a storage unit that stores reference three-dimensional volume data of an examinee obtained by an image pickup device, an ultrasonic probe that is inserted in a body cavity of the examinee and can perform ultrasonic scanning in a radial direction, an ultrasonic image generating unit that generates an ultrasonic tomographic image on the basis of a reflection echo signal from the ultrasonic probe, a position detector that detects a position and a posture of the ultrasonic probe on the basis of a sensor attached to the ultrasonic probe, an image generating unit that generates a scanning position mark representing an ultrasonic scanning position on a tomographic plane parallel to a travel direction of the ultrasonic probe from the reference three-dimensional volume data of the storage unit on the basis of an output of the position detector, and a display unit that displays the ultrasonic tomographic image and the scanning position mark.

11 Claims, 25 Drawing Sheets

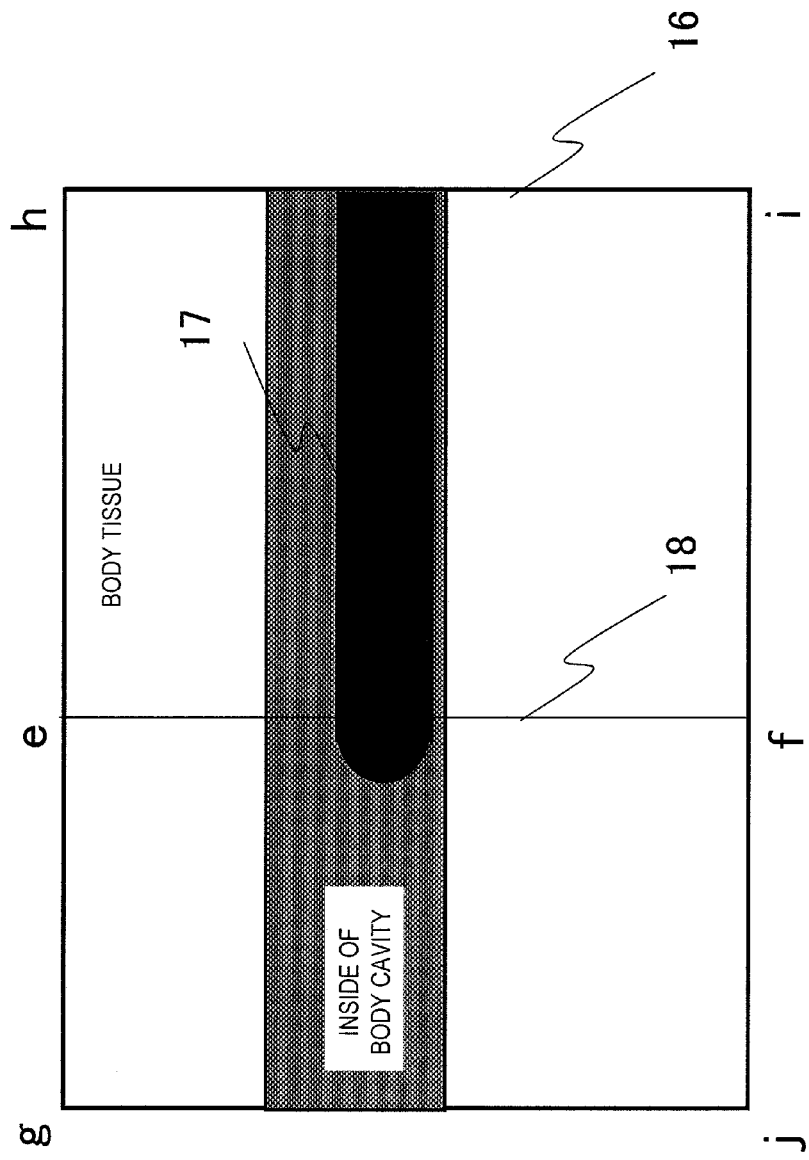

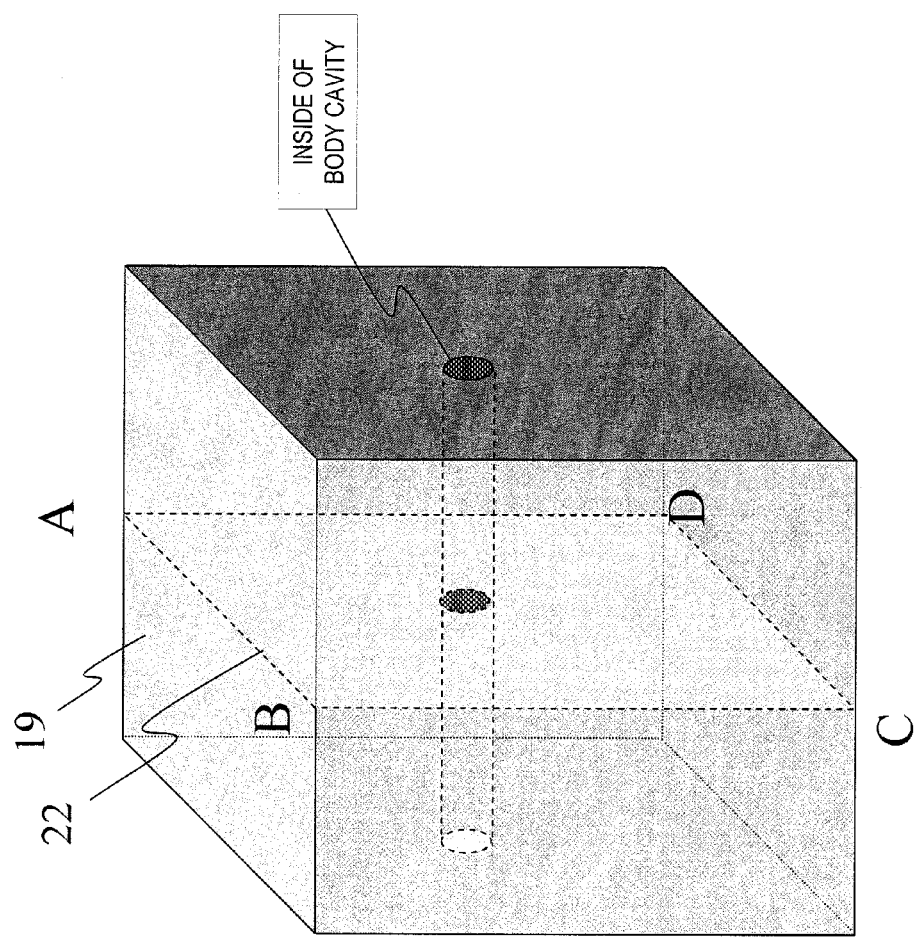

ULTRASONIC DIAGNOSTIC APPARATUS AND METHOD FOR DISPLAYING PROBE OPERATION GUIDE

TECHNICAL FIELD

The present invention relates to an ultrasonic diagnostic apparatus and a method for displaying probe operation guide of the device, and particularly to an ultrasonic diagnostic apparatus for inserting an ultrasonic probe in a body cavity of an examinee and performing ultrasonic scanning in the body cavity, and a method for displaying a probe operation guide.

BACKGROUND ART

A diagnosis based on an ultrasonic diagnostic apparatus has an advantage that an operator such a medical doctor or the like can easily and non-invasively obtain a tomographic image of a diagnostic site on a real-time basis by scanning the diagnostic site with an ultrasonic probe. On the other hand, the ultrasonic tomographic image is more difficult to be observed as shape information from the whole body of an examinee as compared with tomographic images obtained by a magnetic resonance imaging device (hereinafter referred to as MRI device) or an X-ray computer tomographic device (hereinafter referred to as X-ray CT device).

Therefore, there is a requirement of displaying not only an ultrasonic tomographic image, but also an image picked up by an MRI device (hereinafter referred to as MRI image), an image picked up by an X-ray CT device (hereinafter referred to as CT image), plural ultrasonic images (hereinafter referred to as US3D volume data) obtained by picking up an affected site of an examinee with an ultrasonic diagnostic apparatus in advance, etc. all together and making a comprehensive diagnosis while comparing these images with one another.

Therefore, it is known that an image having the same cross-section as an ultrasonic image is reconstructed from the volume data of an MRI image or a CT image picked up in advance by detecting the position and posture of a probe on the basis of a sensor attached to the side surface of the ultrasonic probe as described in Patent Document 1, for example. Accordingly, not only the ultrasonic image, but also an MRI image or a CT image having the same tomographic plane can be synchronously displayed on a monitor, and a diagnosis is made while the correspondence of both the images is grasped on a real-time basis.

Prior Art Document
Patent Document
Patent Document 1: International Laid-open WO2004/ 098414

SUMMARY OF THE INVENTION

Problem to be Solved by the Invention

It is known that a probe is inserted into a body cavity (for example, a gastrointestinal tract area or the like) of an examinee and ultrasonic scanning is performed in the body cavity as in the case of an ultrasonic endoscope, for example. In this case, the operator cannot visually recognize the probe position in the body cavity, and thus it may be difficult for the operator to recognize a site of the inside of the examinee at which an ultrasonic tomographic image is picked up by ultrasonic scanning.

With respect to this point, it is described in the patent document 1 that a 3D body mark of an examinee is generated from a volume data of an MRI image or a CT image, and the 3D body mark and an ultrasonic scan plane are displayed in association with each other, whereby the positional relationship between them can be easily grasped.

However, the technique of the patent document 1 indicates only the ultrasonic scanning position in the examinee, and takes it into no consideration that multilateral information which is not obtained from the ultrasonic tomographic image is provided to an operator in addition to the ultrasonic scanning position, thereby enhancing the diagnosis performance.

The present invention has an object to provide an operator with multilateral information which is not obtained from an ultrasonic scanning position of the inside of an examinee and an ultrasonic tomographic image when a probe is inserted into a body cavity of an examinee and ultrasonic scanning is performed from the body cavity, thereby enhancing diagnostic performance.

Means of Solving the Problem

In order to attain the above object, an ultrasonic diagnostic apparatus according to the present invention comprises a storage unit that stores reference three-dimensional volume data of an examinee obtained by an image pickup device; an ultrasonic probe that is inserted in a body cavity of the examinee and can perform ultrasonic scanning in a radial direction; an ultrasonic image generating unit that generates an ultrasonic tomographic image on the basis of a reflection echo signal from the ultrasonic probe; a position detector that detects a position and a posture of the ultrasonic probe on the basis of a sensor attached to the ultrasonic probe; an image generating unit that generates a scanning position mark representing an ultrasonic scanning position on a tomographic plane parallel to a travel direction of the ultrasonic probe from the reference three-dimensional volume data of the storage unit on the basis of an output of the position detector; and a display unit that displays the ultrasonic tomographic image and the scanning position mark.

Furthermore, a method of displaying a probe operation guide for an ultrasonic diagnostic apparatus according to the present invention comprises: a first step that stores reference three-dimensional volume data of an examinee obtained by an image pickup device by a storage unit; a second step that inserts an ultrasonic probe into a body cavity of the examinee to perform ultrasonic scanning in a radial direction and generates an ultrasonic tomographic image on the basis of a reflection echo signal from the ultrasonic probe by an ultrasonic image generating unit; a third step that detects a position and a posture of the ultrasonic probe on the basis of a sensor attached to the ultrasonic probe by a position detector; a fourth step that generates a scanning position mark representing an ultrasonic scanning position on a tomographic plane parallel to a travel direction of the ultrasonic probe from the reference three-dimensional volume data of the storage unit on the basis of an output of the position detector by an image generating unit; and a fifth step that displays the ultrasonic tomographic image and the scanning position mark by a display unit.

That is, the scanning position mark is an image formed by extracting image data of a tomographic plane paralleling so as to contain a travel direction of the probe from reference three-dimensional volume data such as an MRI image, a CT image or the like, for example, and also is an image on which a mark representing an ultrasonic scanning position (ultrasonic wave transmission/reception direction) is superimposed. Accordingly, by displaying this image together with the ultrasonic tomographic image, an operator can grasp the position in the examinee at which the ultrasonic tomographic image is picked up. Furthermore, the scanning position mark is an image of a tomographic plane which is cut out from the reference three-dimensional volume data. Therefore, for example, useful information such as a tumor or the like to be observed can be provided to an operator from an angle different from the ultrasonic tomographic image, whereby diagnosis performance can be enhanced.

Effect of the Invention

According to the present invention, when a probe is inserted into the body cavity of an examinee and ultrasonic scanning is performed from the body cavity, multilateral information which is not obtained from the ultrasonic scanning position of the inside of the examinee and the ultrasonic tomographic image can be provided to an operator and thus the diagnosis performance can be enhanced.

BRIEF DESCRIPTION OF THE DRAWINGS

FIG. 3 is a conceptual diagram showing a travel-direction reference tomographic image generated by a first embodiment.

FIG. 6A shows a display style of a third embodiment.

EMBODIMENTS FOR CARRYING OUT THE INVENTION

Figure 1:
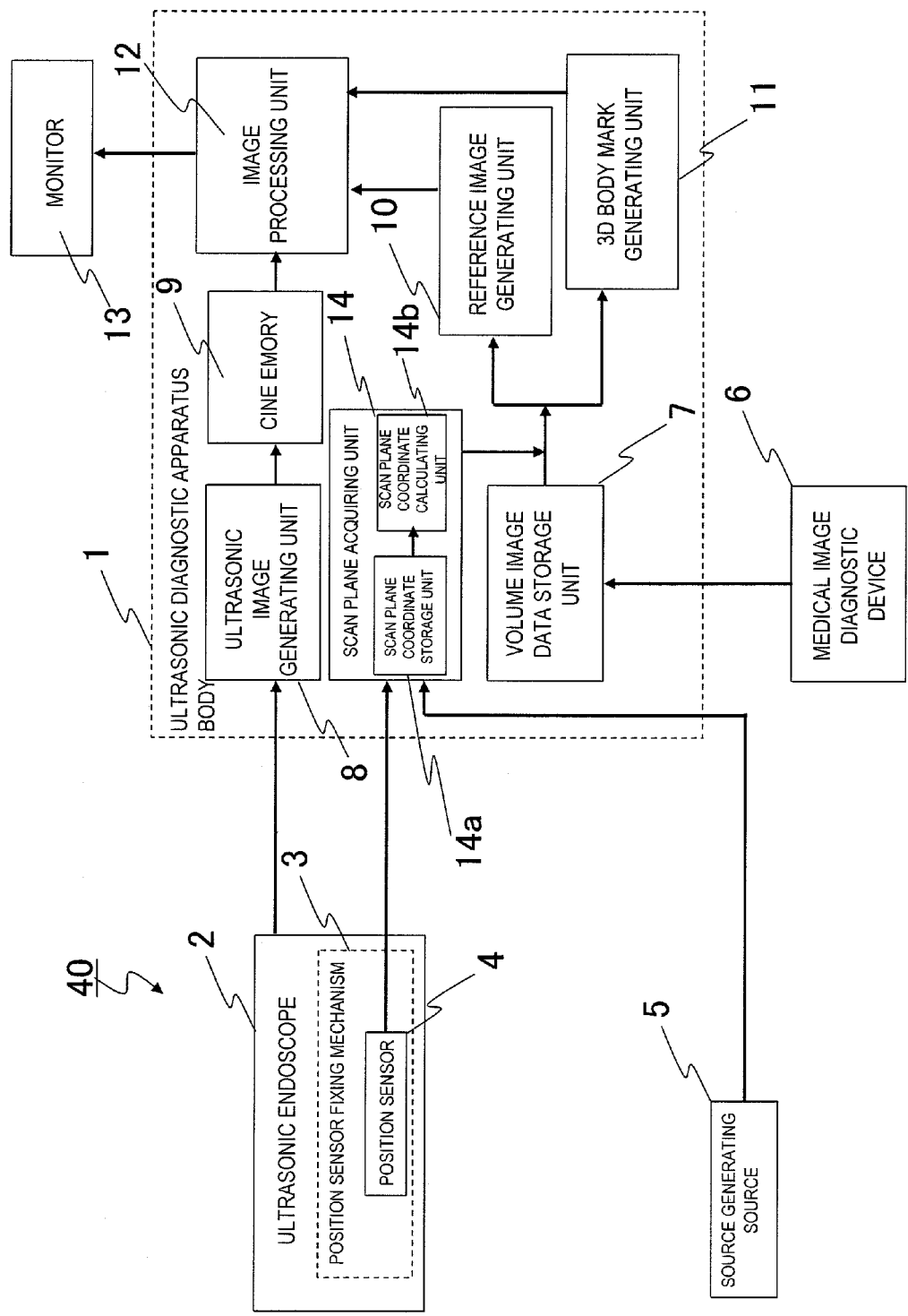
FIG. 1 is a diagram showing the overall schematic construction of an ultrasonic diagnostic apparatus according to an embodiment.

Embodiments of an ultrasonic diagnostic apparatus to which the present invention is applied will be described. In the following description, parts having the same functions are represented by the same reference numerals, and the duplicative description thereof is omitted.

FIG. 1 is a diagram showing the overall schematic construction of an ultrasonic diagnostic apparatus according to this embodiment. An ultrasonic diagnostic apparatus 40 comprises an ultrasonic diagnostic apparatus body 1 and an ultrasonic endoscope 2.

The ultrasonic endoscope 2 is inserted in a body cavity of an examinee to transmit/receive ultrasonic waves in a radial direction in the body cavity. In this embodiment, the ultrasonic endoscope is adopted as an example, however, a probe such as a transesophageal probe or the like, etc. may be arbitrarily used insofar as they are inserted in a body cavity of an examinee and transmit/receive ultrasonic waves in the body cavity, for example. Furthermore, the ultrasonic endoscope 2 of this embodiment is of a radial scan (electronic, mechanical) type. However, it is not limited to this type, but a convex type, a linear type may be used.

A position sensor 4 such as a magnetic sensor or the like which is used to detect the position and posture of the ultrasonic endoscope 2 is fixed in the ultrasonic endoscope 2 by a position sensor fixing mechanism 3 serving as a fixing unit. A source generating source 5 for generating a source such as magnetic field or the like in a coordinate system containing the examinee is disposed nearby a bed on which the examinee lies down for example, and the position and posture of the ultrasonic endoscope 2 are detected by the position sensor 4 and the source generating source 5.

The ultrasonic diagnostic apparatus body 1 is divided into a system for generating an ultrasonic tomographic image and a system for generating a reference tomographic image. The system for generating an ultrasonic image comprises an ultrasonic image generating unit 8 for generating an ultrasonic tomographic image on the basis of a reflection echo signal of ultrasonic waves measured by the ultrasonic endoscope 2, a cine-memory 9 for storing plural frames of generated ultrasonic tomographic images, etc.

The system for generating a reference image comprises a volume image data storage unit 7 for storing reference three-dimensional volume data of an examinee which are obtained by a medical image diagnostic device 6 such as an X-ray CT device, an MRI device, an ultrasonic diagnostic apparatus or the like, a scan plane acquiring unit 14 for detecting the position and posture of the ultrasonic endoscope 2 on the basis of output signals of the position sensor 4 and the source generating source 5 fixed to the ultrasonic endoscope 2 and calculates the ultrasonic tomographic plane, etc. of the ultrasonic endoscope 2 on the basis of the detected position and posture of the ultrasonic endoscope 2, and a reference image generating unit 10 for generating a same cross-section reference tomographic image (second reference tomographic image) having the same tomographic plane as an ultrasonic tomographic image and a probe travel-direction reference tomographic image (first reference tomographic image) from reference three-dimensional volume data of the volume image data storage unit 7 on the basis of the ultrasonic tomographic plane calculated in the scan plane acquiring unit 14, etc.

The system further has a 3D body mark generating unit 11 for generating a three-dimensionally visualized image, an image processor 12 for associating an ultrasonic tomographic image stored in the cine-memory 9 with a reference tomographic image generated in the reference image generating unit 10, a monitor 13 serving as a display unit for displaying the ultrasonic tomographic image and the reference tomographic image which are associated with each other in the image processor 12, etc.

The ultrasonic diagnostic apparatus body 1 has a mechanism which can easily input the reference three-dimensional volume data of the examinee picked up by the X-ray CT device or the MRI device, US3D volume data picked up by another ultrasonic diagnostic apparatus, etc. When the volume data is input into the ultrasonic diagnostic apparatus body 1, the volume data is stored in the volume image data storage unit 7 in the device.

Of course, the ultrasonic diagnostic apparatus body 1 may be directly connected to the x-ray CT device, the MRI device or the other ultrasonic diagnostic apparatus through an input/output interface (not shown) to receive volume data, and may store the volume data into the volume image data storage unit 7 in the ultrasonic diagnostic apparatus. Furthermore, the volume data may be stored in the volume image data storage unit 7 in the ultrasonic diagnostic apparatus through a network or through a portable recording medium such as an USB memory or the like. The respective constituent elements of the ultrasonic diagnostic apparatus body 1 will be described hereunder.

The reference image generating unit 10 extracts the image data of the examinee corresponding to position information processed in the scan plane acquiring unit 14 from the volume image data storage unit 7, and generates the reference tomographic image. The generated reference tomographic image is processed in the image processing unit 12 so as to be displayed on the monitor 13 of the ultrasonic diagnostic apparatus, and then it is displayed on the monitor 13 of the ultrasonic diagnostic apparatus.

Figure 2:
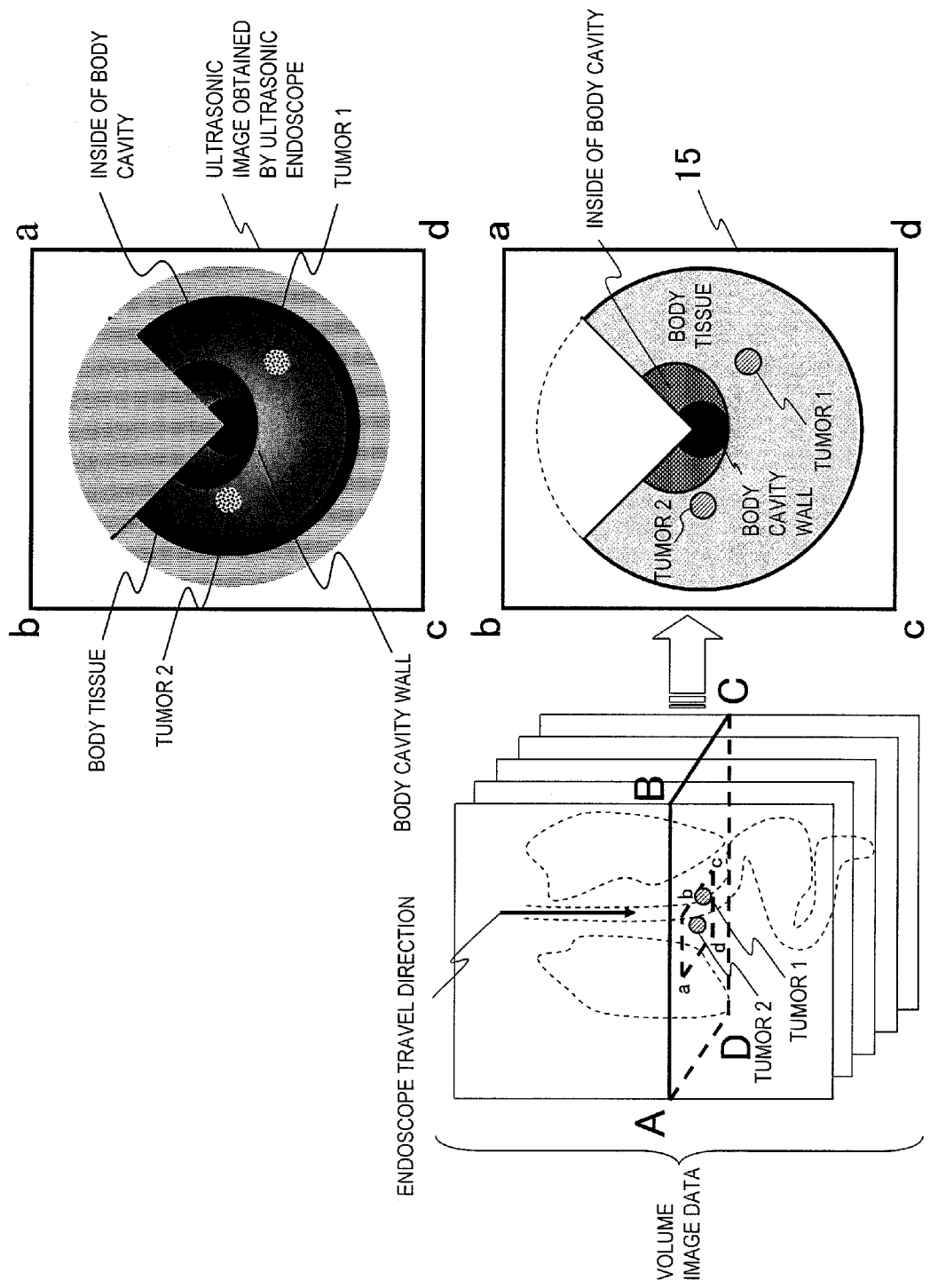
FIG. 2 is a, diagram showing the concept of extracting a reference image having the same cross-section as an ultrasonic tomographic image from three-dimensional volume data.

FIG. 2 shows the concept of extracting a reference image having the same cross-section as an ultrasonic tomographic image from three-dimensional volume data. The three-dimensional volume data are data comprising plural image data, and the image data having the same cross-section (for example, ABCD plane) as the ultrasonic tomographic image from the three-dimensional volume data are extracted. Furthermore, the reference image generating unit 10 has a function of magnifying/demagnifying the reference image in accordance with the scale of enlargement (magnification) of the ultrasonic tomographic image generated in the ultrasonic image generating unit 8, and displaying the reference image at the same magnification as the ultrasonic tomographic image. For example, FIG. 2 shows the concept of magnifying and displaying only an area (ABCD plane) of interest out of the ABCD plane of the reference image.

Furthermore, as shown in FIG. 2, the reference image generating unit 10 has a function of extracting an out-of-visual-field area in accordance with the visual field of the ultrasonic tomographic image obtained by the ultrasonic endoscope 2, and reducing the brightness of the reference tomographic image corresponding to the area (same-cross-section reference tomographic image 15 having the same tomographic plane as the ultrasonic tomographic image). By such a function, the correspondence between the ultrasonic tomographic image and the reference tomographic image is clear, and the operator can easily grasp the association relationship between both the tomographic images.

The reference image generating unit 10 changes the image size and frame rate of the reference tomographic image in accordance with the motion of the ultrasonic endoscope 2, whereby the reconstructing speed of the reference tomographic image can be changed. That is, when the motion of the ultrasonic endoscope is quick, the frame rate supersedes the image quality and the reference tomographic image is drawn at high speed. Conversely, when the motion speed of the ultrasonic endoscope is low, the image quality supersedes the frame rate and the reference image is reconstructed and drawn. Accordingly, the ultrasonic tomographic image follows the motion of the ultrasonic endoscope 2 and the reference tomographic image can be drawn.

The 3D body mark generating unit 11 has a function of drawing a three-dimensionally visualized image of an area being imaged by using reference three-dimensional volume data. Furthermore, it has a function of calculating the position, etc. of a part scanned by the ultrasonic endoscope 2 in the scan plane acquiring unit 14, a scan plane obtained on the basis of the calculation result is displayed with semitransparent color and superimposed.

Accordingly, the operator can three-dimensionally grasp the positional relationship between the examinee and the scan plane of the ultrasonic endoscope 2. A well-known method such as volume rendering, surface rendering or the like may be applied to the three-dimensional visualization processing described above.

The image processor 12 processes the reference tomographic image generated in the reference image generating unit 10 and the ultrasonic tomographic image generated in the ultrasonic image generating unit 8 to display these tomographic images on the monitor 13 of the ultrasonic diagnostic apparatus. For example, the ultrasonic tomographic image and the reference tomographic image may be displayed to be arranged side by side, or the reference tomographic image maybe made semitransparent and superimposed on the ultrasonic image. When the reference tomographic image is superimposed, the ultrasonic tomographic image and the reference tomographic image can be easily compared with each other on one image. Additionally, the images generated in the cinememory 9, the reference image generating unit 10 and the 3D body mark generating unit 11 may be arbitrarily combined with one another and displayed.

Next, with respect to the ultrasonic diagnostic apparatus according to this embodiment, a manner of detecting the position of the scan plane of the ultrasonic tomographic image picked up by the ultrasonic endoscope 2 will be described. The ultrasonic tomographic plane is implemented by the position sensor 4 such as a magnetic sensor or the like which is fixed in the ultrasonic endoscope 2, the source generating source 5 which is disposed, for example, beside the bed or the like on which the examinee lies down and generates a source such as magnetic field or the like in a coordinate system containing the examinee, the scan plane acquiring unit 14 provided to the ultrasonic diagnostic apparatus body 1, etc. as shown in FIG. 1.

The position sensor 4 and the source generating source 5 are electrically connected to the scan plane acquiring unit 14. The scan plane acquiring unit 14 has a scan plane coordinate storage unit 14A and a scan plane coordinate calculating unit 14B, and it acquires position information such as the position/slope angle, etc. of the ultrasonic endoscope 2 obtained by the position sensor 4 and the source generating source 5, calculates the three-dimensional position, the slope angle, etc. of the ultrasonic endoscope 2 and also calculates the scan plane of the ultrasonic endoscope. The calculated scan cross-section is processed in the image processor 12, and associated with the ultrasonic image generated in the ultrasonic image generating unit 8.

The position detection based on magnetic field is described as an example of the position detection. However, the present invention is not limited to this method, and various kinds of well-known position detecting methods may be used insofar as they are usable.

Through each processing described above, the ultrasonic diagnostic apparatus body 1 can generate a reference tomographic image having the same cross-section, magnification and field of vision as the ultrasonic tomographic image obtained by the ultrasonic endoscope 2, and generate a composite image thereof. This composite image and the 3D body mark are displayed on the same monitor 13 of the ultrasonic diagnostic apparatus. Accordingly, an operator can easily grasp the correspondence between the ultrasonic tomographic image and the reference tomographic image, and execute an effective and comprehensive diagnosis, on an examinee by comparing these images.

The image processing step described above is shown in the patent document 1, and in this ultrasonic diagnostic apparatus, the ultrasonic tomographic image and the reference tomographic image in an ultrasonic diagnosis of a gastrointestinal tract area or the like can be displayed by using the same image processing.

In addition to the conventional technique as described above, the ultrasonic diagnosis device according to this embodiment provides an operator with an ultrasonic tomographic image, a reference image having the same cross-section as the ultrasonic tomographic image and multilateral information which is not obtained from a conventional three-dimensional body mark, thereby enhancing the diagnosis performance. The feature portion of the ultrasonic diagnostic apparatus according to this embodiment will be described by using embodiments.

Embodiment 1

According to this embodiment, a tomographic image of a cross-sectional plane extending parallel so as to contain a travel direction of the ultrasonic endoscope 2 from the reference three-dimensional volume data by the reference image generating unit 10 is generated, and a travel-direction reference tomographic image is also generated by superimposing a scan position mark representing an ultrasonic scanning position on the tomographic image concerned. In other words, an image which passes through the center axis of the ultrasonic endoscope 2 and is perpendicular to a radial scan plane is extracted and generated from reference three-dimensional volume data.

FIG. 3 is a conceptual diagram showing the travel-direction reference tomographic image generated according to this embodiment. An illustration 17 representing the ultrasonic endoscope 2 being inserted and a scanning position mark 18 representing the ultrasonic scanning position (a line EF representing the position of the reference tomographic image 15 having the same tomographic plane) are displayed on a travel-direction reference tomographic image 16 (ghij plane).

Figure 4A:
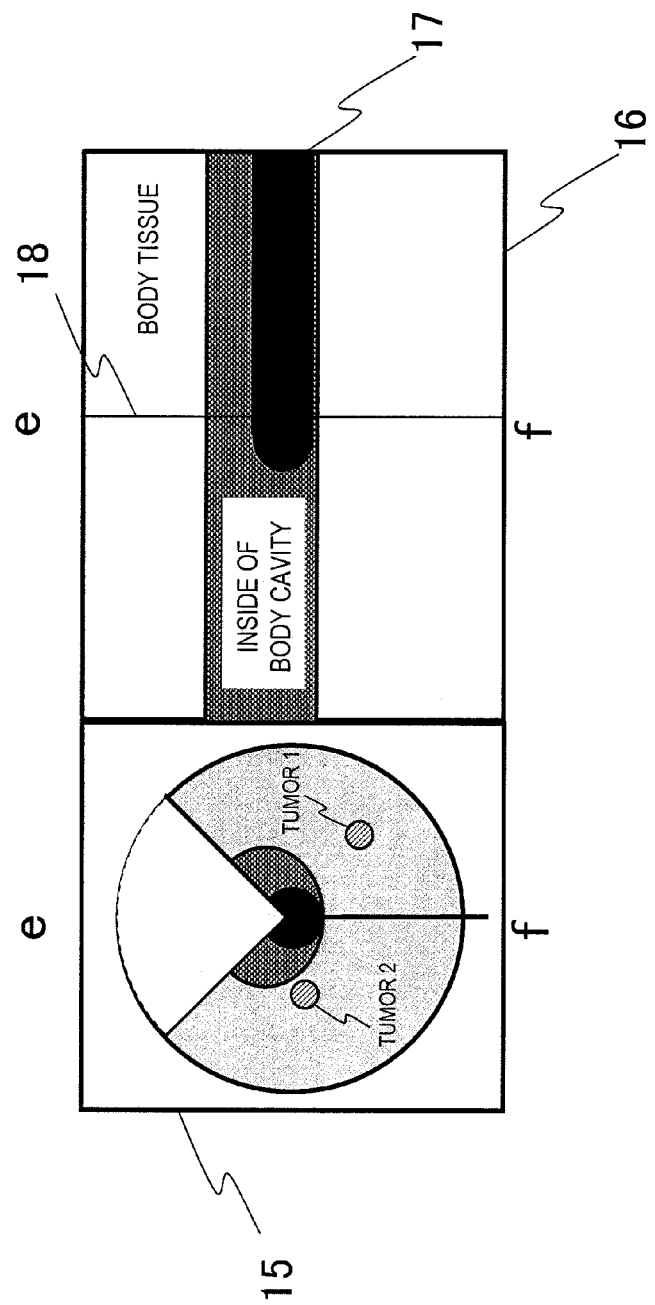
FIG. 4A shows a display style of the first embodiment.

For example, as shown in FIG. 4A, the reference tomographic image 15 having the same cross-section and the travel-direction reference tomographic image 16 are displayed in combination, whereby not only the tomographic plane of an examinee viewed from the travel direction (insertion direction) of the ultrasonic endoscope 2, but also information of the examinee viewed from a different angle side can be provided to an operator.

Figure 4B:
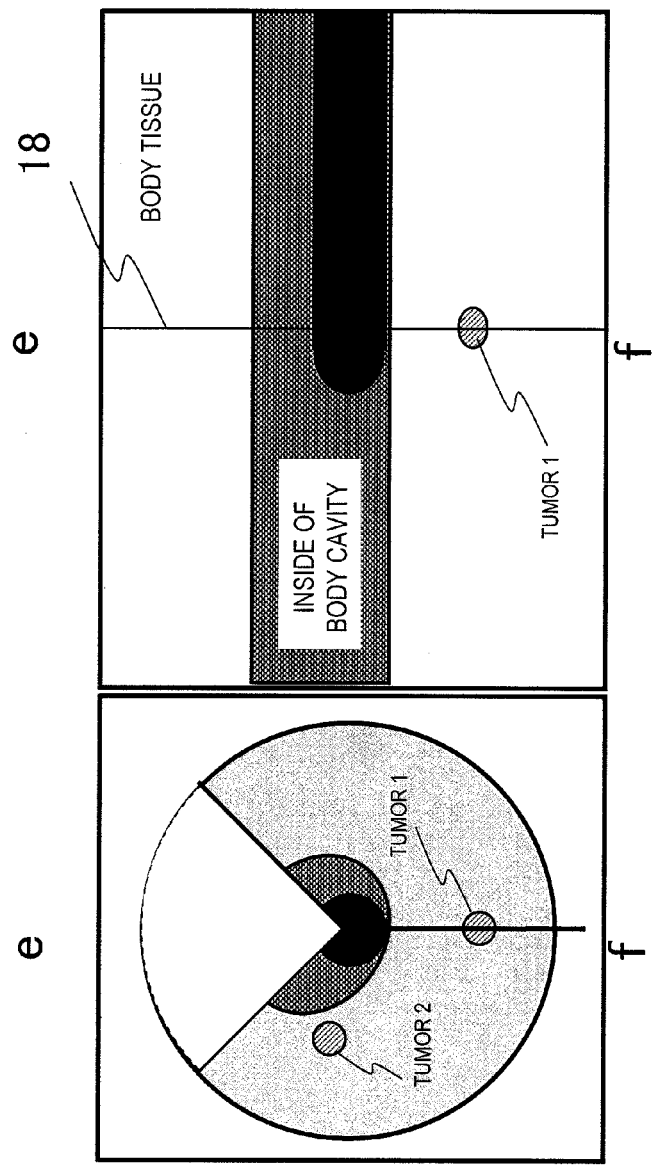
FIG. 4B shows a display style of the first embodiment.
Figure 4C:
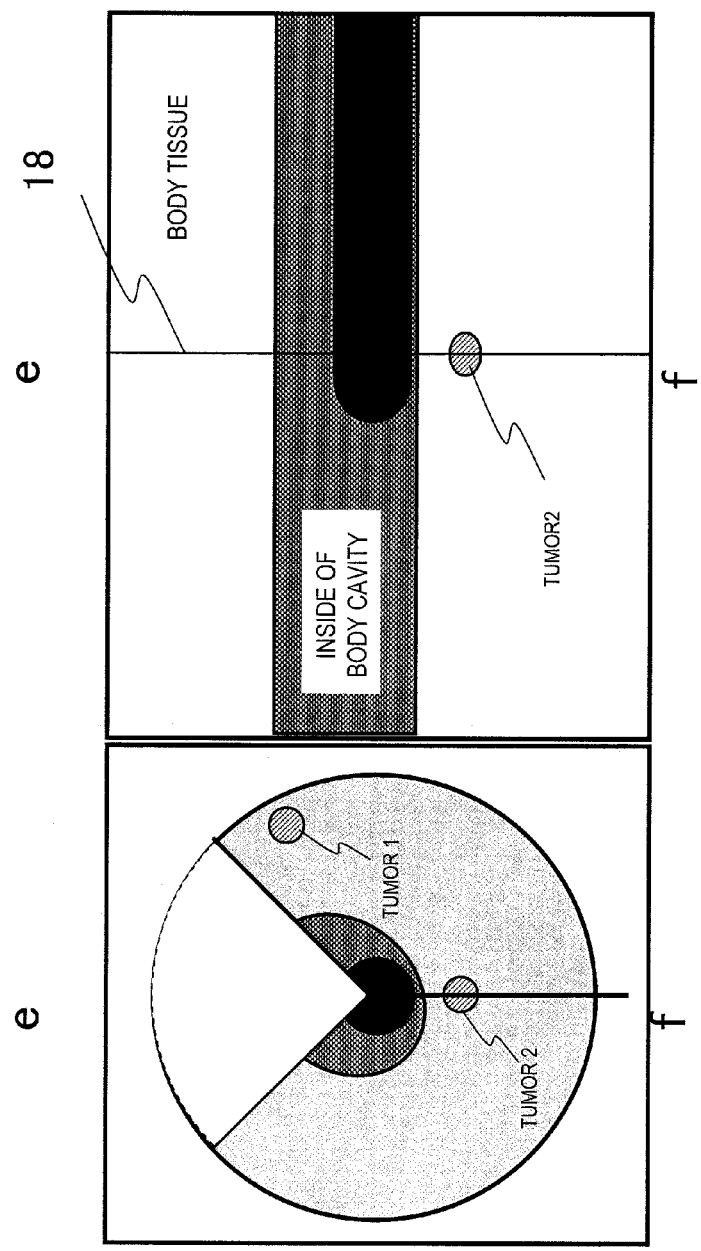
FIG. 4C shows a display style of the first embodiment.

As shown in FIGS. 4B and 4C, when the ultrasonic endoscope 2 is rotated on the center axis of the endoscope, the reference tomographic image 15 having the same tomographic plane and the travel-direction reference tomographic image 16 can be updated in connection with this rotation. Accordingly, a site which is desired to be observed, such as a tumor or the like, can be checked on the basis of both the images while rotating the ultrasonic endoscope 2. Therefore, the position of the tumor is more clarified, and the tumor can be more easily captured.

Embodiment 2

This embodiment is the same as the first embodiment in that the travel-direction reference tomographic image 16 is generated, however, this travel-direction reference tomographic image 16 and the ultrasonic tomographic image are displayed in combination.

Figure 5:
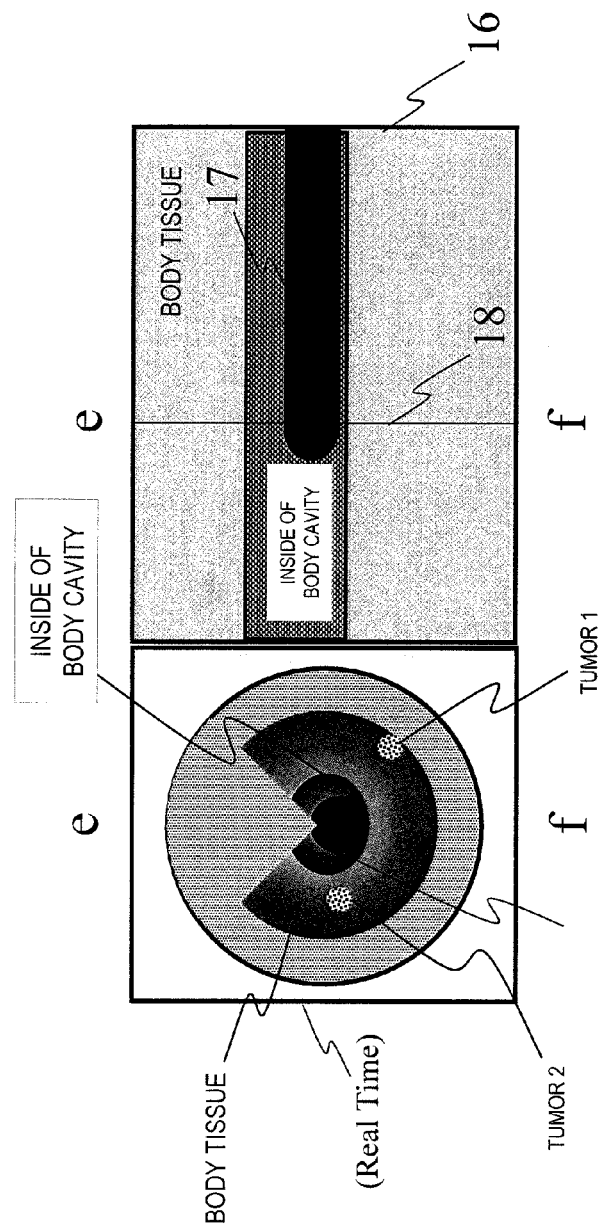
FIG. 5 shows a display style of a second embodiment.

As shown in FIG. 5, the ultrasonic tomographic image obtained by the ultrasonic endoscope 2 and the travel-direction reference tomographic image 16 are displayed in association with each other. Accordingly, an operator can grasp the ultrasonic tomographic image and the position in the examinee at which the ultrasonic tomographic image is picked up.

Furthermore, the travel-direction reference tomographic image 16 is an image of a tomographic plane which is cut out from reference three-dimensional volume data. Therefore, useful information of a tumor or the like which is desired to be observed can be provided to an operator from an angle which is different from an ultrasonic tomographic image. As a result, the diagnosis performance can be enhanced.

Still furthermore, according to this embodiment, the travel-direction reference tomographic image 16 is displayed ahead of the ultrasonic tomographic image being displayed with respect to the travel direction of the endoscope. Therefore, the operator can grasp the travel direction of the endoscope in the body cavity of the examinee, and thus can easily insert/pull the ultrasonic endoscope. Accordingly, from the examinee's standpoint, a risk that the inside of the body cavity is damaged by inserting/pulling the ultrasonic endoscope can be reduced.

Furthermore, the ultrasonic tomographic image obtained by the ultrasonic endoscope 2, the reference tomographic image 15 having the same tomographic plane and the travel-direction reference tomographic image 16 maybe simultaneously displayed in association with one another. Still furthermore, a point-of-view may be provided in the body cavity so that a virtual optical image is created from reference three-dimensional volume data and displayed as if it is viewed from the ultrasonic endoscope 2.

Embodiment 3

According to this embodiment, a three-dimensional body mark is generated on the basis of reference three-dimensional volume data of an examinee, and also the three-dimensional body mark is cut by a tomographic plane which is parallel to the travel direction of the ultrasonic endoscope 2 and contains the travel direction, and a scanning position mark representing the ultrasonic scanning position is superimposed on the cut-out three-dimensional body mark to generate a half body mark.

Figure 6B:
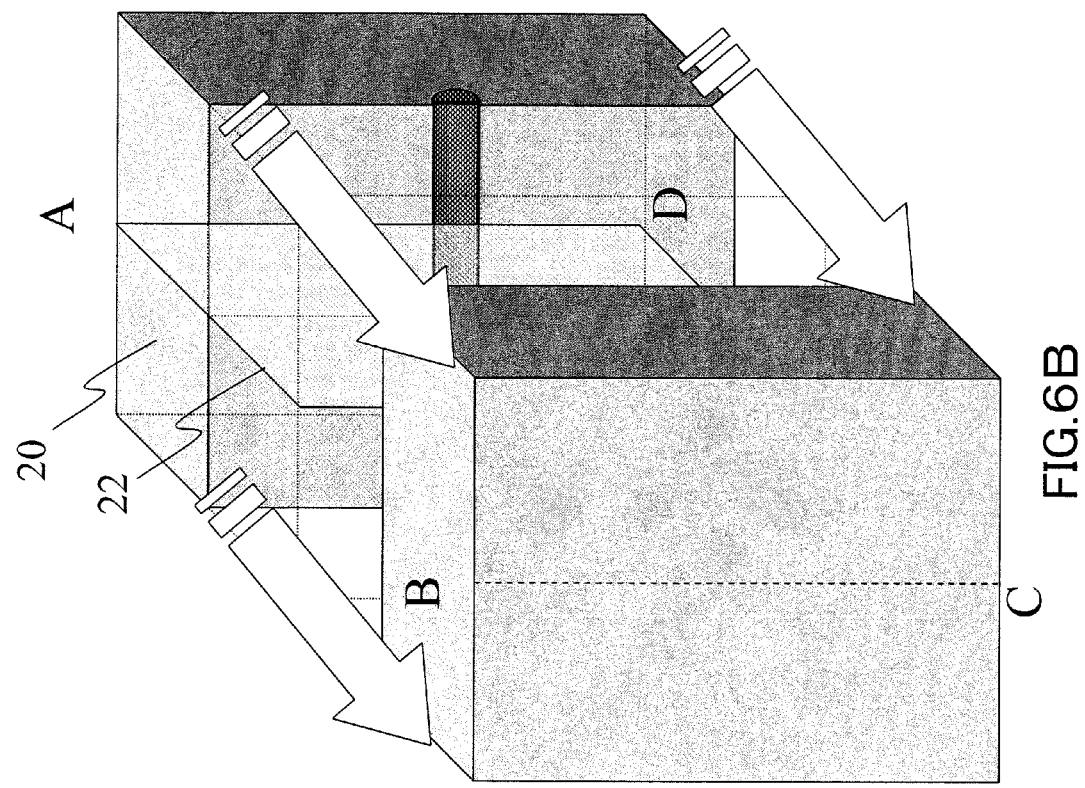
FIG. 6B shows a display style of the third embodiment.
Figure 6C:
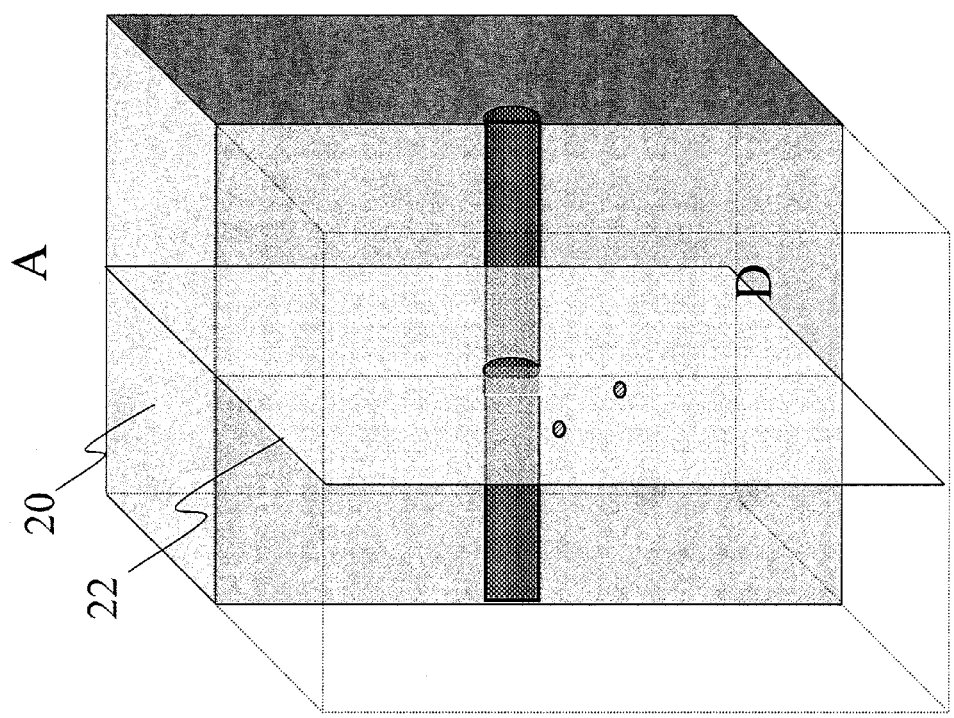
FIG. 6C shows a display style of the third embodiment.

FIG. 6A is a diagram showing the concept of generating the half body mark, and is a conceptual diagram showing a three-dimensional body mark 19 and an ultrasonic scanning plane 22 (ABCD plane). FIG. 6B is a conceptual diagram showing that the three-dimensional body mark 19 is cut by a tomographic plane passing in the travel direction of the ultrasonic endoscope 2. The body mark is divided into two parts by cutting as described above, whereby one half body mark 20 containing an AD line is generated as shown in FIG. 6C, for example. In this case, with respect to the other half body mark having a BC line, an outline portion thereof may be displayed by a dashed line or the like or it may be never displayed.

Figure 6D:
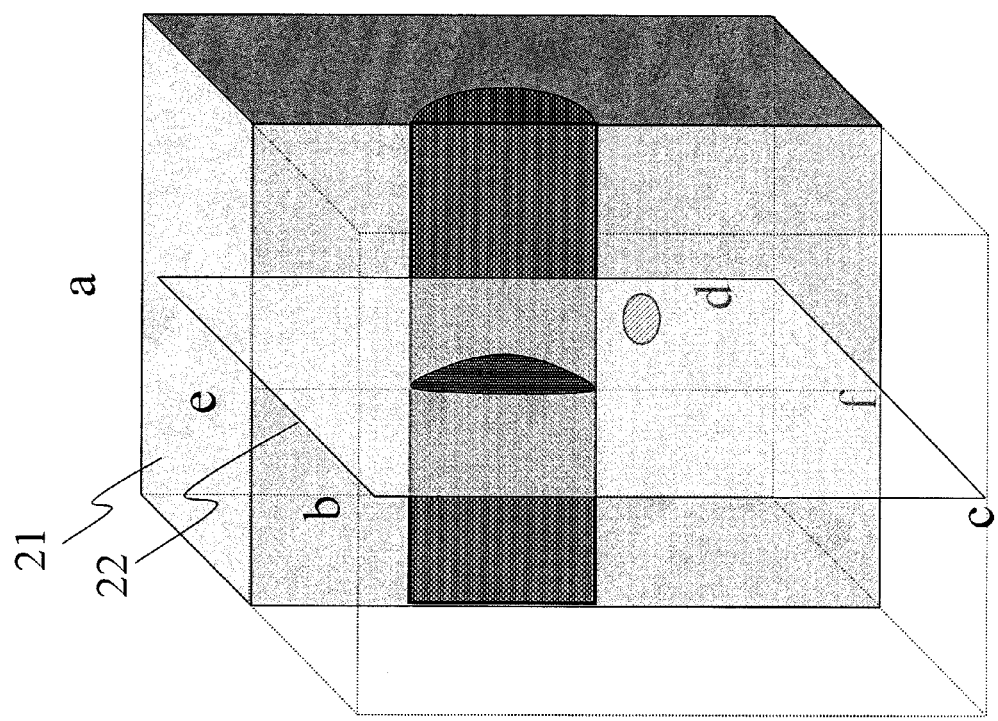
FIG. 6D shows a display style of the third embodiment.

The half body mark 20 is not constructed by surface rendering, but by volume rendering. The half body mark 20 may be displayed with being enlarged/reduced. For example, a half body mark 21 shown in FIG. 6D is obtained by enlarging and displaying an area having a tumor in the half body mark 20.

Figure 6E:
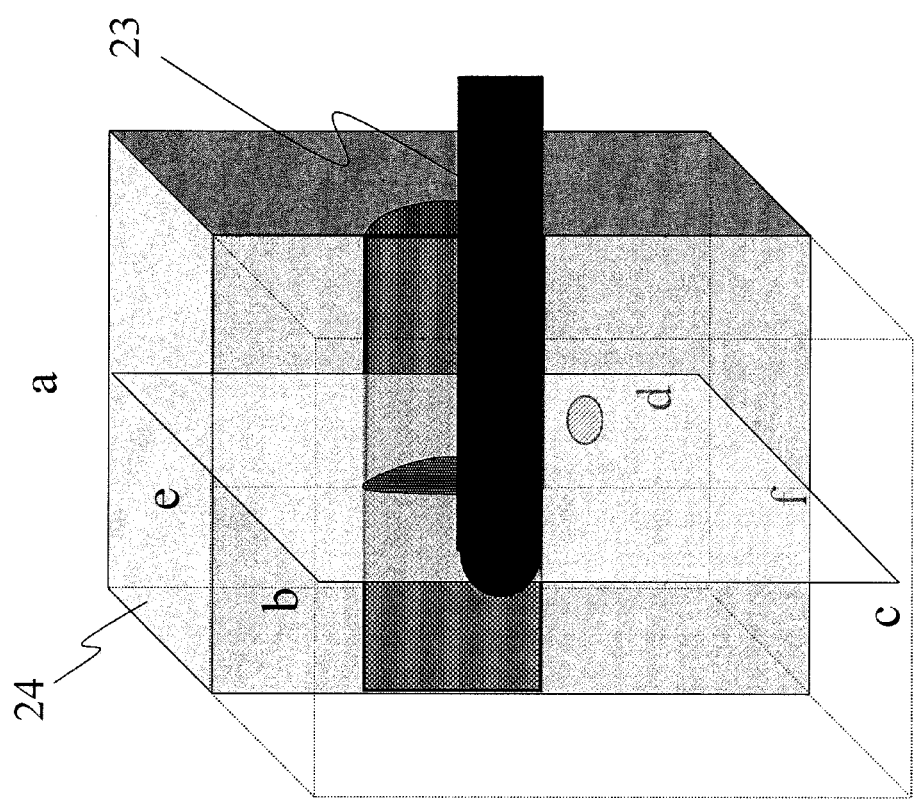
FIG. 6E shows a display style of the third embodiment.

With respect to these half body marks 20, 21, an illustration 23 representing the ultrasonic endoscope 2 may be generated and displayed on the body marks 20, 21. FIG. 6E is a diagram showing a half body mark 24 generated while the illustration 23 representing the ultrasonic endoscope 2 is superimposed on the half body mark 24.

Figure 6F:
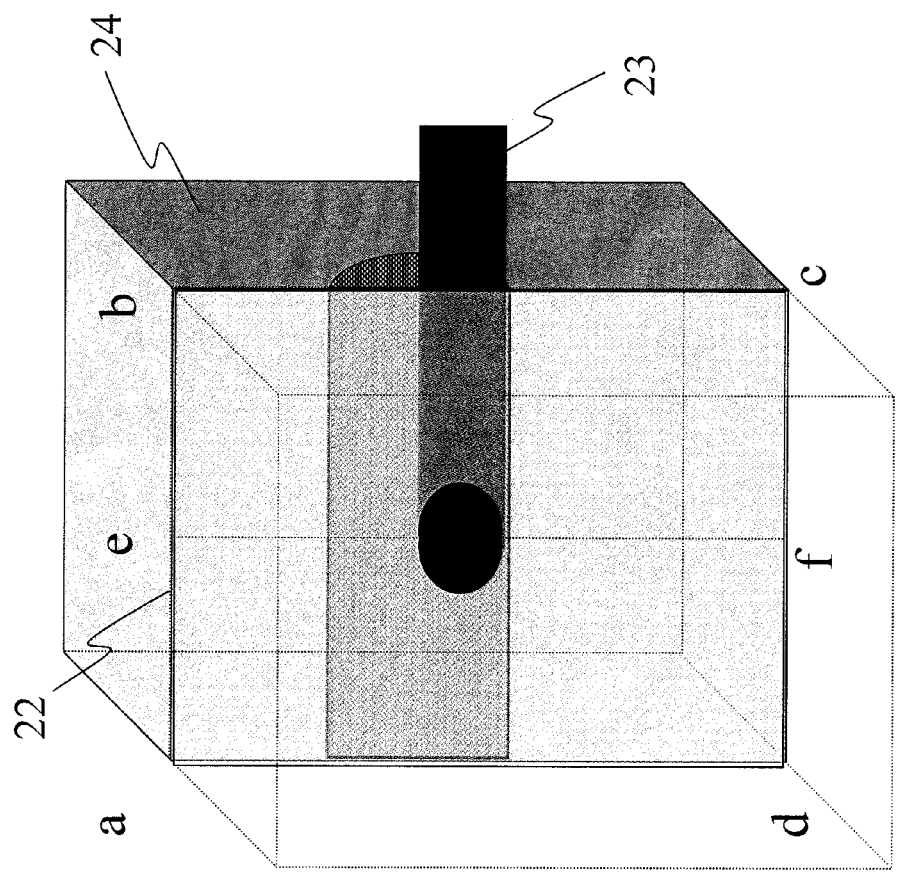
FIG. 6F shows a display style of the third embodiment.

When the ultrasonic endoscope 2 is moved, the display of the illustration 23 representing the ultrasonic scanning plane 22 and the ultrasonic endoscope 2 can be moved while following the motion of the ultrasonic endoscope 2. FIG. 6F is a diagram showing a case where the tip of the ultrasonic endoscope 2 faces the left side with respect to the travel direction in the body cavity, for example. In such a case, the display of the illustration 23 representing the ultrasonic scanning plane 22 and the ultrasonic endoscope 2 varies as shown in FIG. 6F.

The thus-generated half body mark is displayed together with the ultrasonic tomographic image. According to this embodiment, an operator can grasp the position in the examinee at which the ultrasonic tomographic image is picked up. Furthermore, the half body mark contains useful information of a tumor or the like which is desired to be observed from an angle different from the ultrasonic tomographic image, and thus the diagnosis performance can be enhanced by displaying this. In addition, a point of view is provided in the half body mark, and a virtual optical image is created and displayed as if it is viewed from the ultrasonic endoscope 2, whereby the diagnosis performance can be also enhanced.

Embodiment 4

In addition to the third embodiment, the other half body mark is displayed in this embodiment. That is, the third embodiment displays the one cut-out half body mark, however, the other half body mark paired with the one three-dimensional body mark can be generated and displayed in this embodiment while the scanning position mark representing the ultrasonic scanning position is superimposed on the other three-dimensional body mark.

Figure 7A:
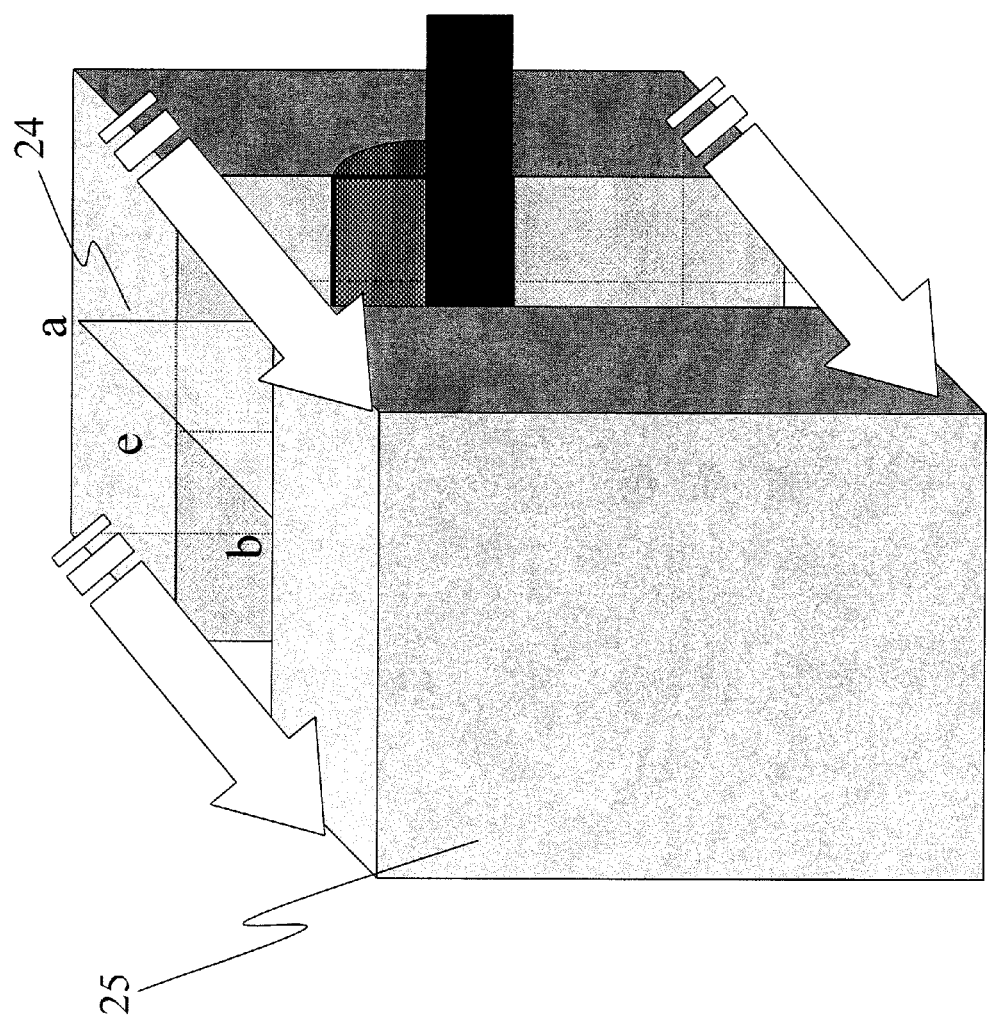
FIG. 7A shows a display style of a fourth embodiment.
Figure 7B:
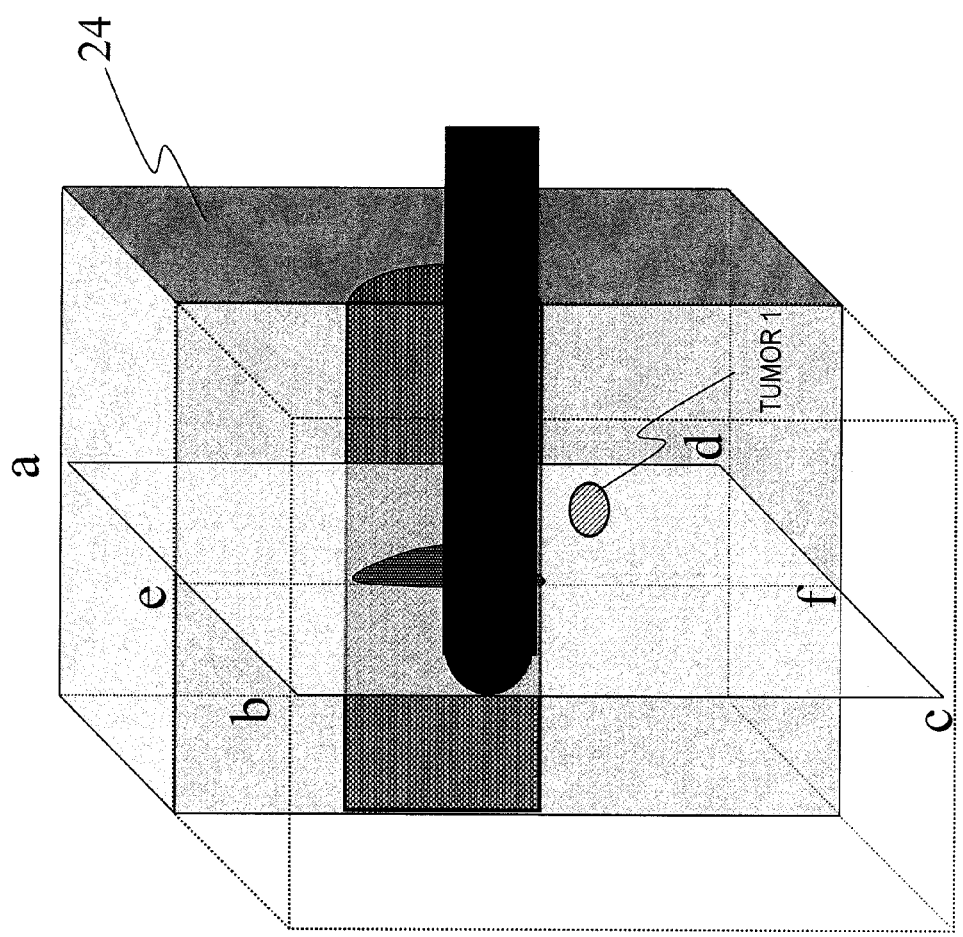
FIG. 7B shows a display style of the fourth embodiment.
Figure 7C:
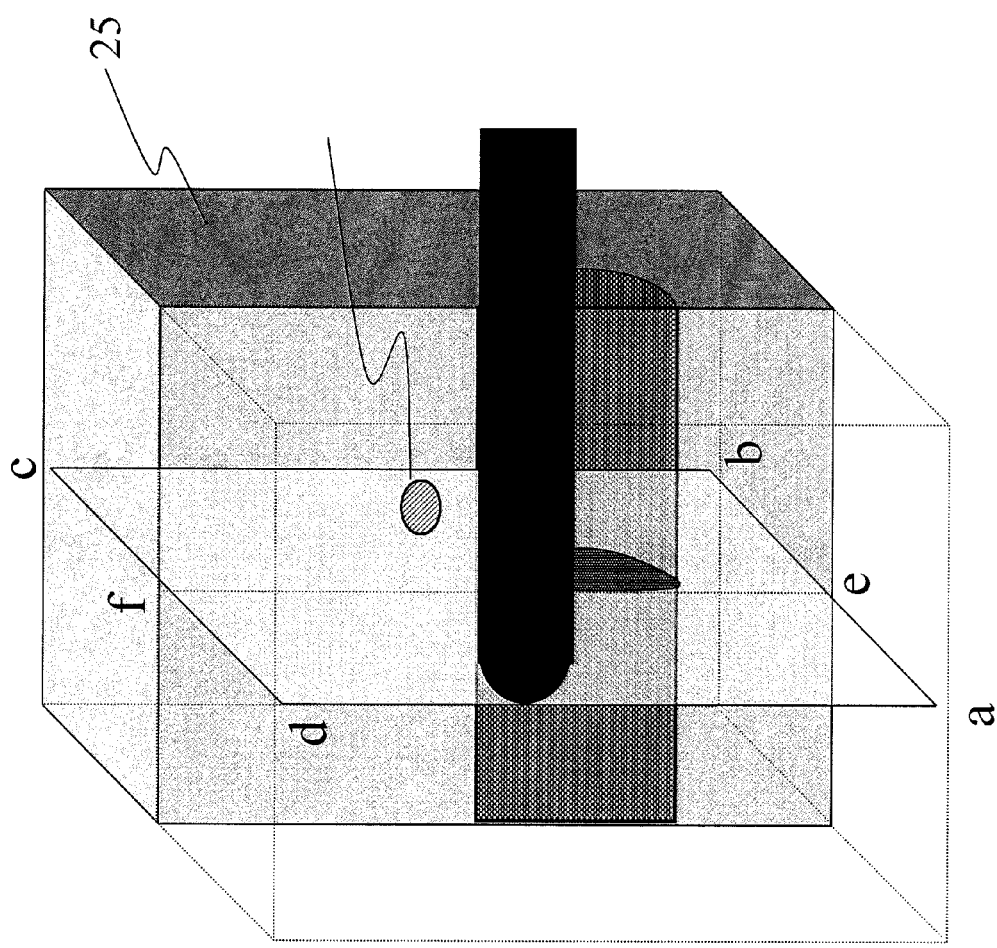
FIG. 7C shows a display style of the fourth embodiment.

FIG. 7 is a diagram showing an example in which the one body mark and the other body mark are displayed. FIG. 7A is a conceptual diagram showing a state that the three-dimensional body mark is cut. FIG. 7B is a diagram showing one half body mark containing a line AD. FIG. 7C is a diagram showing the other half body mark containing a line BC. As shown in FIG. 7C, the other half body mark 25 is reversed and displayed so that the cut surface thereof is turned up. In FIG. 7C, the other half body mark 25 is also reversed and displayed in the vertical direction, however, it may not be reversed with respect to the vertical direction. These half body marks are displayed together with at least the ultrasonic tomographic image.

As described above, the cut surfaces of both the body marks are displayed so that the operator can see the cut surfaces (the cut surfaces are turned up), whereby useful information for diagnosis contained in each of the body marks (for example, a tumor 1 contained in one half body mark 24, a tumor 2 contained in the other half body mark 25, etc.) can be multilaterally provided to the operator.

Embodiment 5

According to this embodiment, a plane representing the position of a display cross-section of a reference image (hereinafter referred to as reference cut plane 26) and an illustration 23 on the half body mark are displayed while they are superimposed on each other.

Figure 8A:
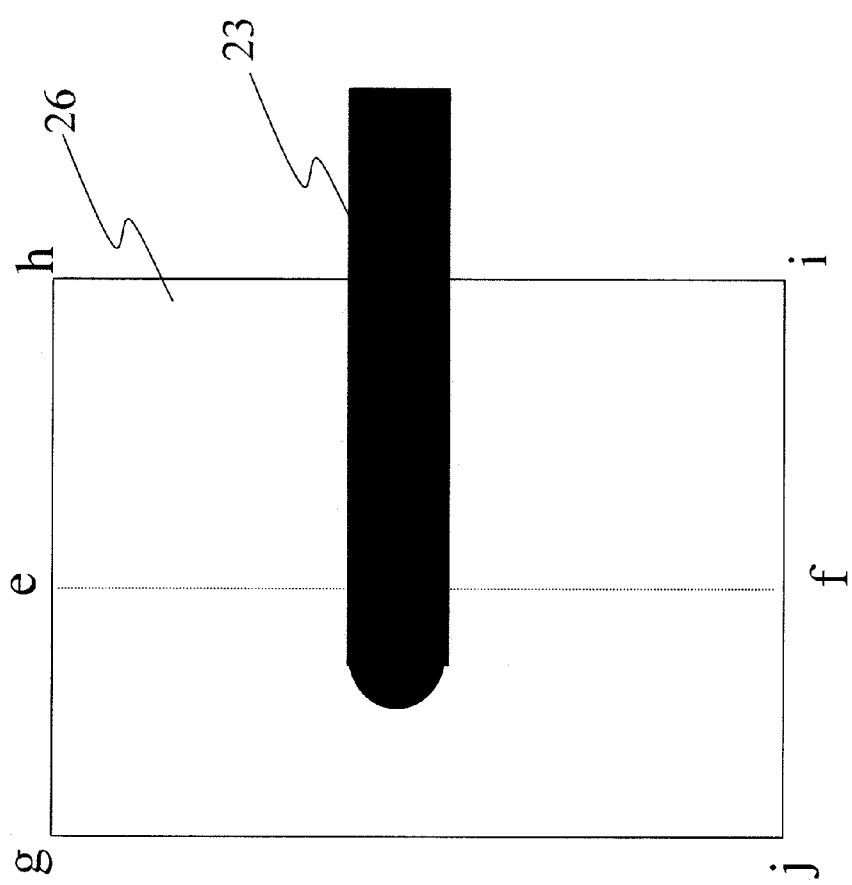
FIG. 8A shows a display style of a fifth embodiment.
Figure 8B:
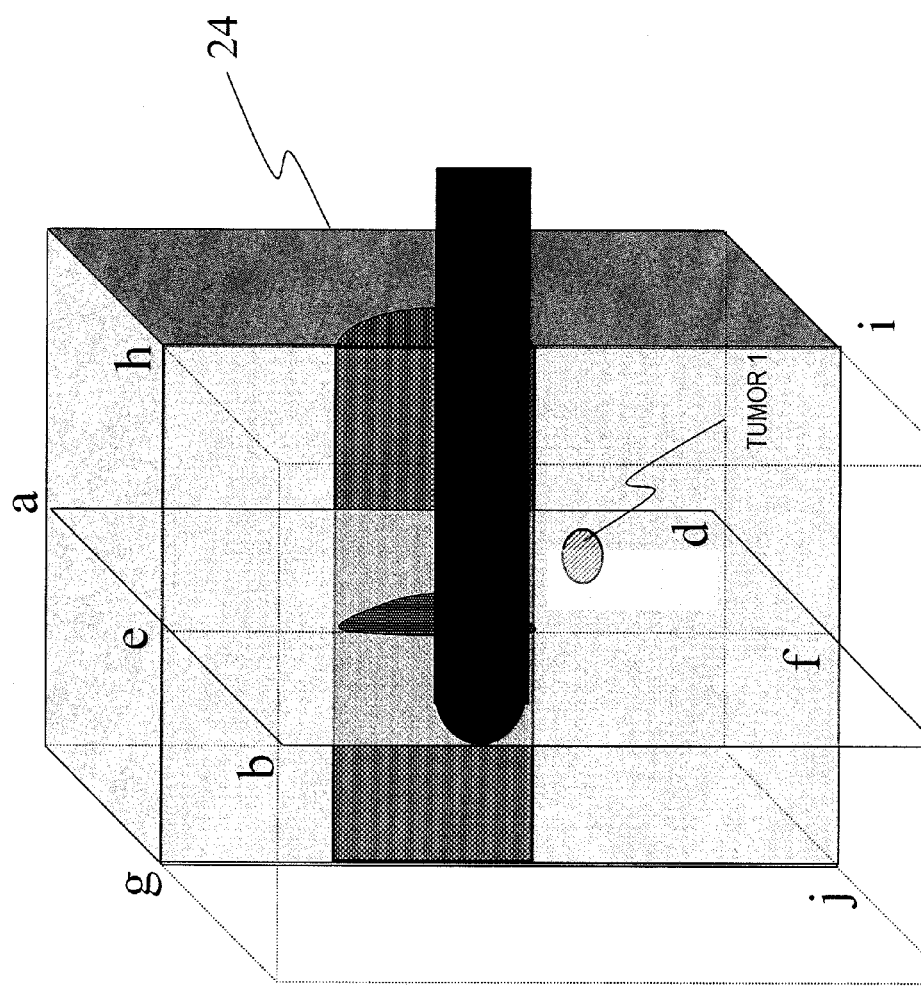
FIG. 8B shows a display style of the fifth embodiment.
Figure 8C:
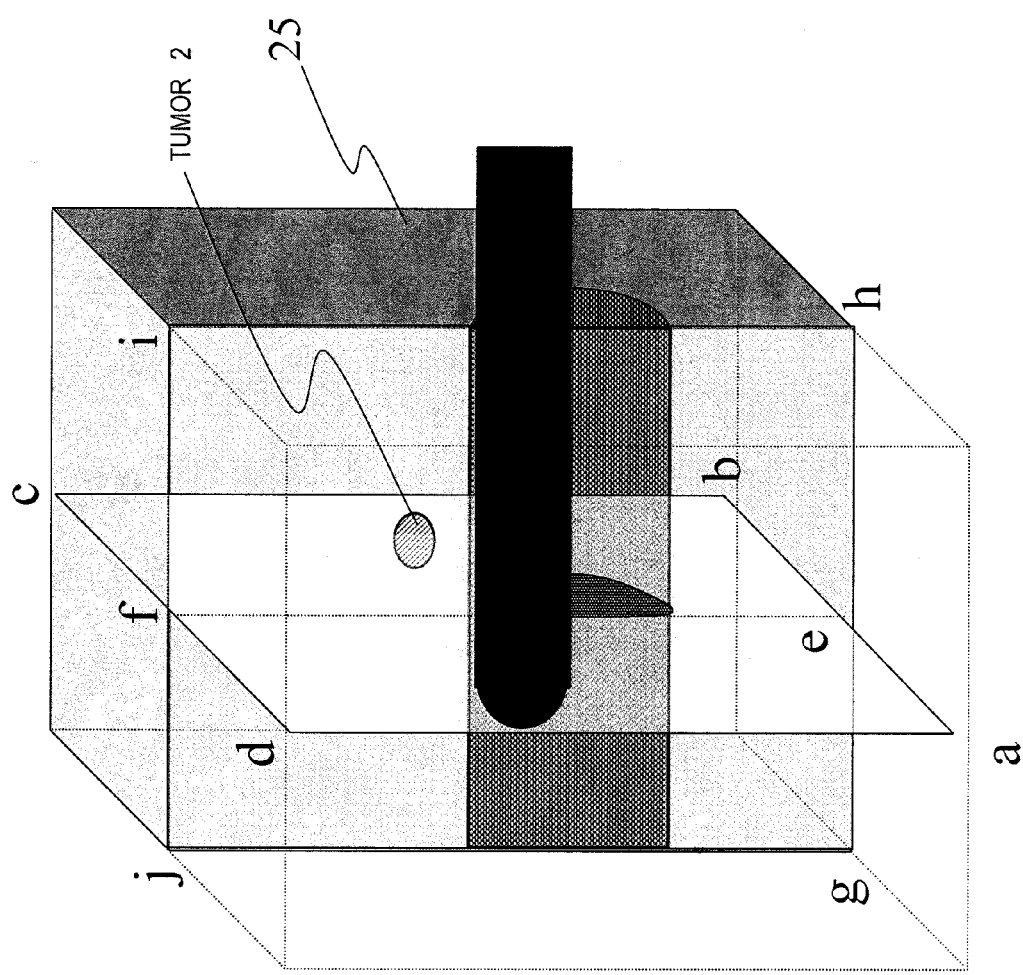
FIG. 8C shows a display style of the fifth embodiment.

Specifically, when an orthogonal cross-section is displayed on a reference image or when an ultrasonic tomographic image and the travel-direction reference tomographic image 16 are displayed, the reference cut plane 26 and the ultrasonic scanning plane 22 representing the position of an ultrasonic image as shown in FIG. 8A can be displayed with different colors so as to be discriminable from each other (FIG. 8B). In addition, the reference cut plane 26 and the ultrasonic scanning plane 22 representing the position of the ultrasonic image maybe displayed on the other half body mark 25 with different colors so as to be discriminable from each other as shown in FIG. 8C.

Furthermore, when the ultrasonic endoscope being used is a biplane adaptive ultrasonic endoscope, the cross-section displayed by the reference cut plane 26 can be displayed by an ultrasonic image, and in this case, the cross-section can be displayed while the color of the reference cut plane 26 is set to the same as the scan plane representing the position of the ultrasonic image.

Figure 9:
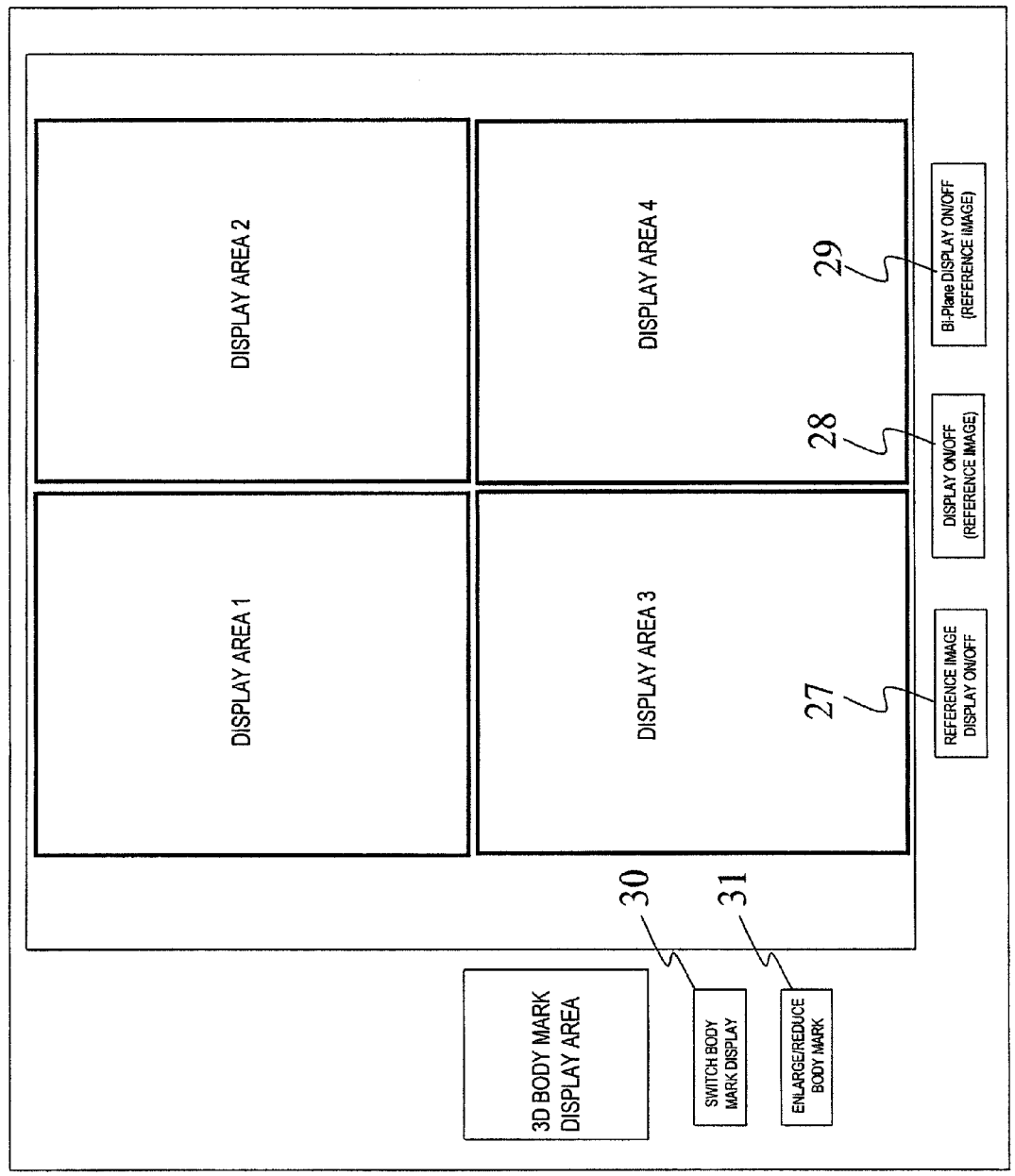
FIG. 9 is a diagram showing an example of display areas and operating buttons of a monitor.

An example in which each style of the embodiments 1 to 5 is displayed on the monitor 13 will be described hereunder. FIG. 9 is a diagram showing an example of a display area and an operation button of the monitor. As shown in FIG. 9, the monitor 13 is provided with display areas 1 to 4 for displaying various kinds of images.

Furthermore, on the ultrasonic device or the monitor are provided a reference image display ON/OFF button 27, a linear display ON/OFF (reference image) button 28 for switching display/non-display of the travel-direction reference tomographic image 16 every pushing, and a Bi-Plane display ON/OFF (reference image) button 29 for switching display/non-display of a biplane display on a reference tomographic image comprising the same-cross-section reference image 15 and the travel-direction reference tomographic image 16 every pushing. Furthermore, a display switching button 30 of a body mark and a button 31 for switching enlargement/reduction of the body mark are provided.

Figure 10A:
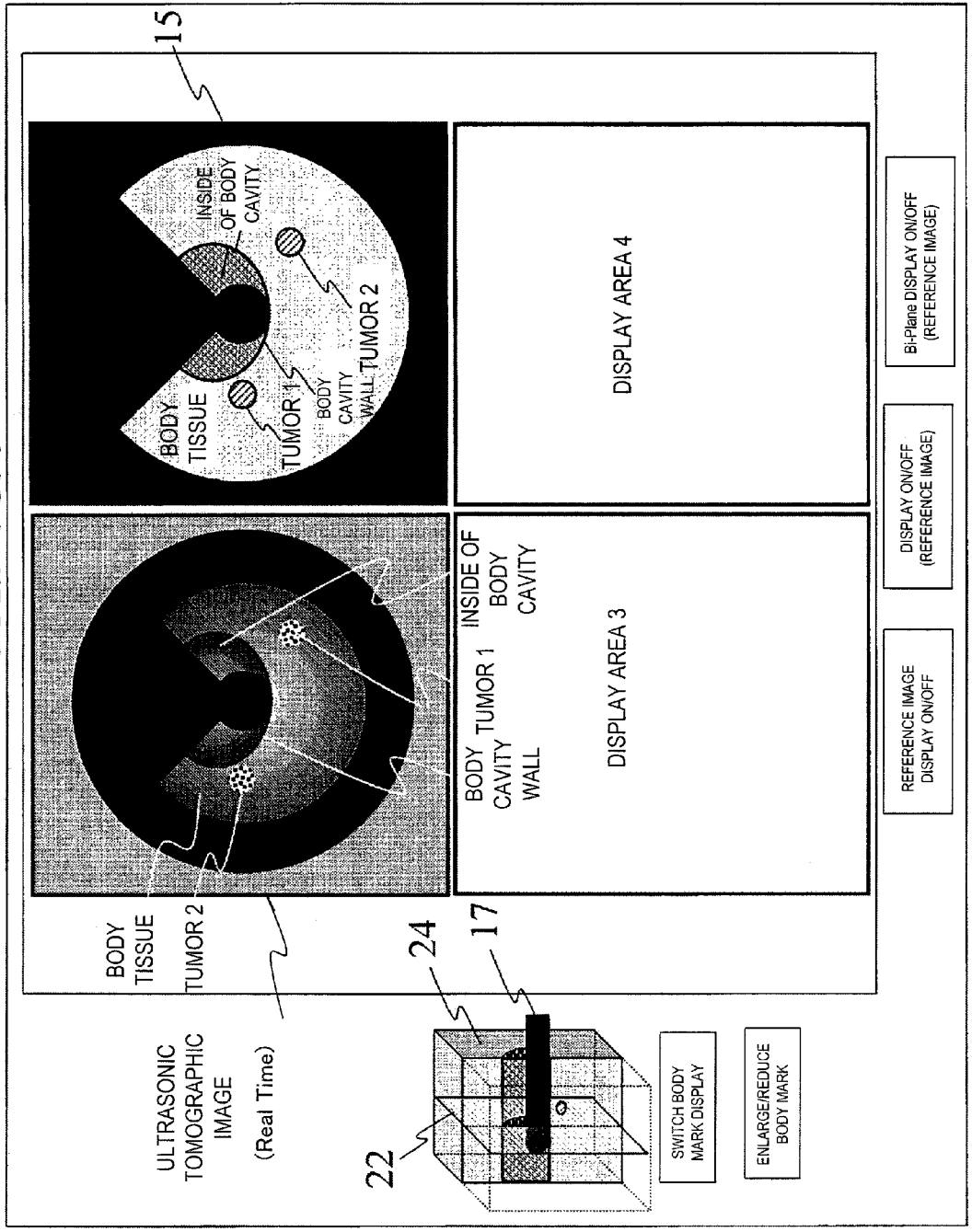
FIG. 10A is a diagram showing a display example of the monitor.

When the reference image display ON/OFF button 27 is pushed, the screen shown in FIG. 10A is displayed as an initial screen. On the initial screen are displayed an ultrasonic tomographic image, the same-cross-section reference tomographic image 15 and the one half body mark 24. Accordingly, the ultrasonic scanning position in the examinee can be checked on the basis of the one half body mark 24 while the ultrasonic tomographic image and the same-cross-section reference tomographic image 15 are compared with each other.

Figure 10B:
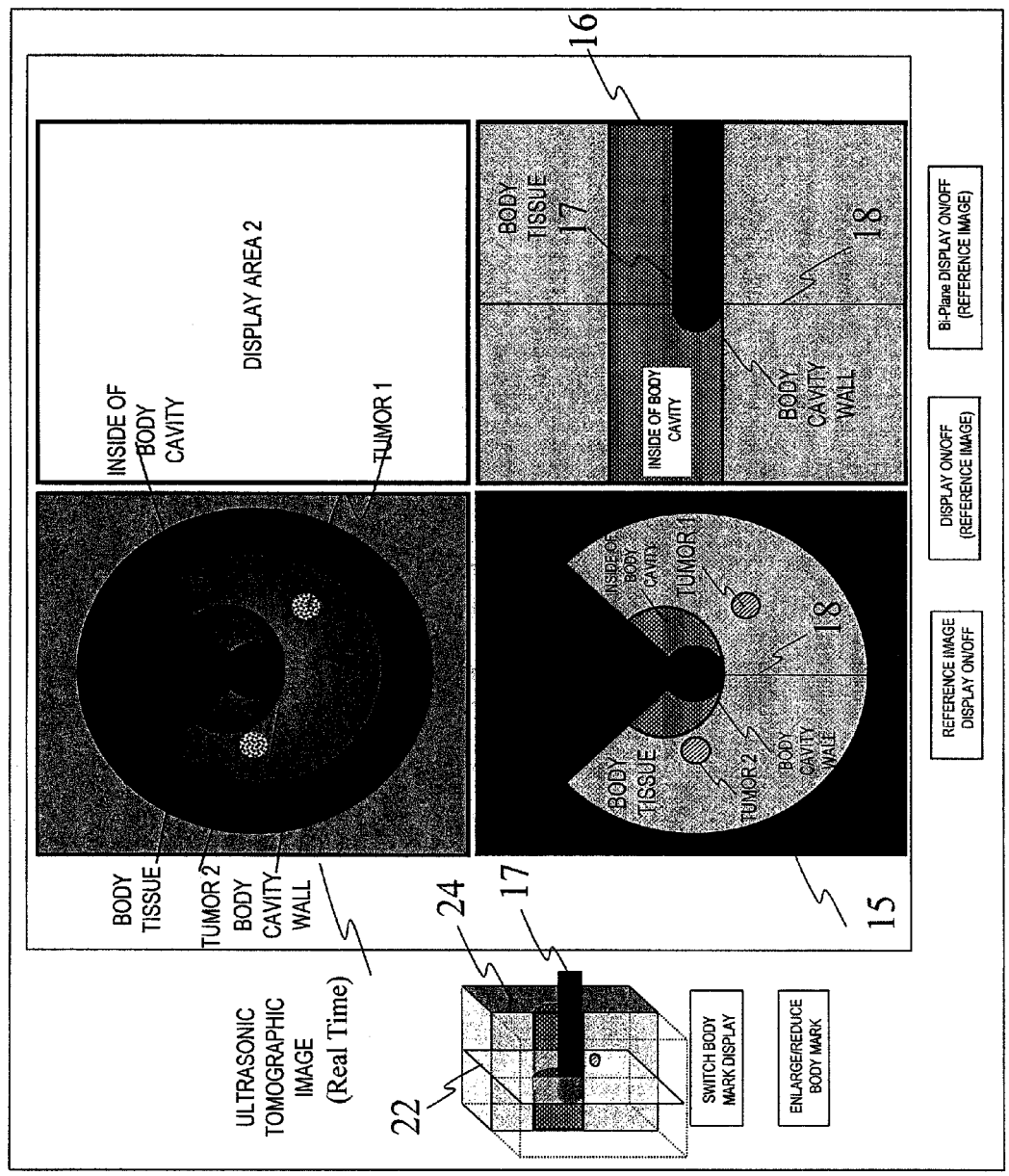
FIG. 10B is a diagram showing a display example of the monitor.

When the linear display ON/OFF button 28 is pushed, the display is switched to the screen shown in FIG. 10B. On this screen are displayed the ultrasonic tomographic image, the same-cross-section reference tomographic image 15, the travel-direction reference tomographic image 16 and the one half body mark 24. Accordingly, the position in the examinee at which these images are picked up and the tomographic plane information viewed from an angle different from these images can be grasped while diagnosis, etc. are performed by comparing the ultrasonic tomographic image and the same-cross-section reference image, so that the diagnosis performance can be further enhanced.

Figure 10C:
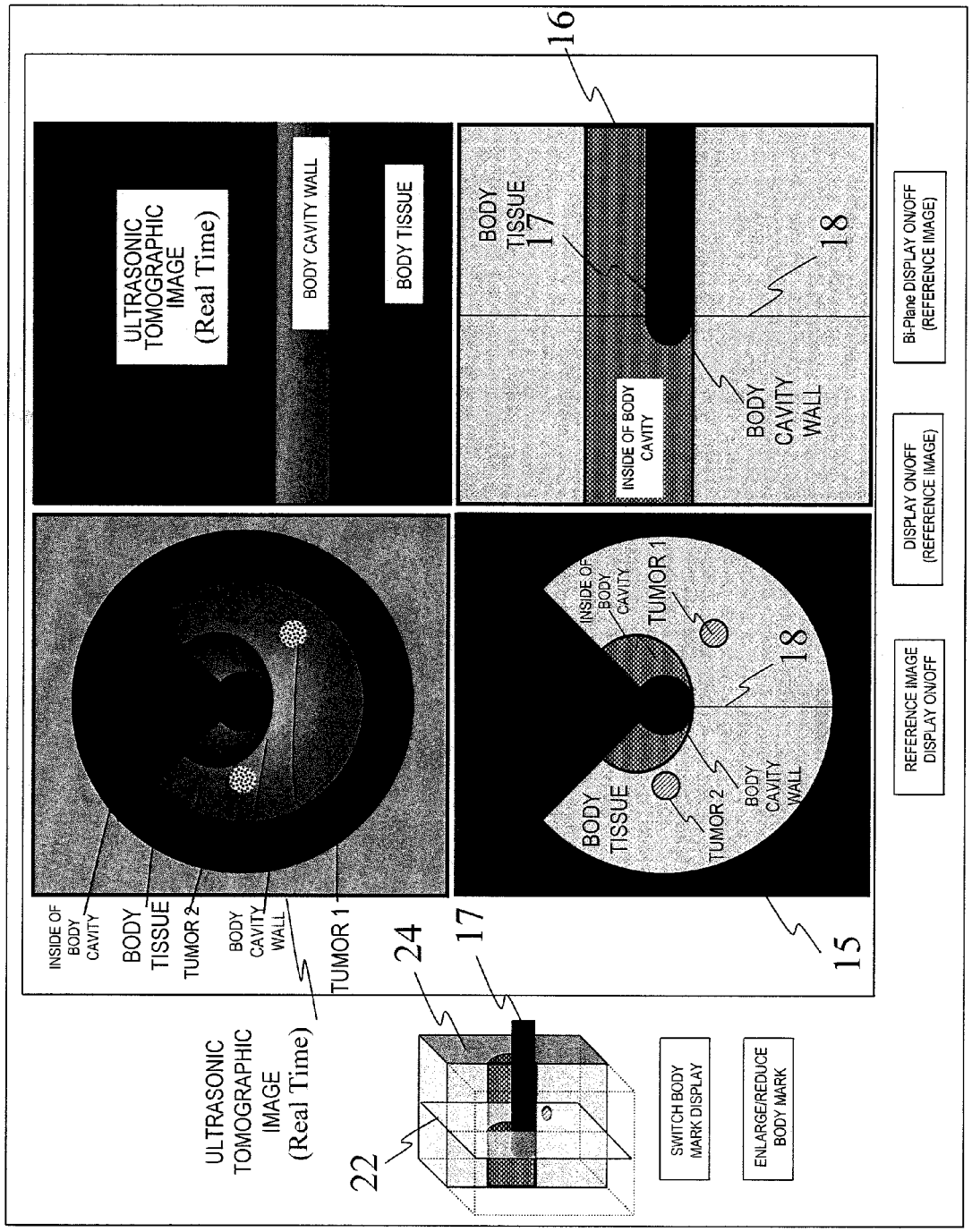
FIG. 10C is a diagram showing a display example of the monitor.

Furthermore, when the ultrasonic endoscope 2 is a probe adaptive to Bi-Plane which also performs ultrasonic scanning in a direction perpendicular to the radial direction, upon pushing of the Bi-Plane display ON/OFF button 29, the display is switched to the screen shown in FIG. 10C. On this screen are displayed the ultrasonic tomographic image in the radial direction, the ultrasonic tomographic image in the direction perpendicular to the radial direction, the same-cross-section reference tomographic image 15, the travel-direction reference tomographic image 16 and the one half body mark 24.

Both the ultrasonic tomographic image in the radial direction and the same-cross-section reference tomographic image 15 and both the ultrasonic tomographic image in the direction perpendicular to the radial direction and the travel-direction reference tomographic image 16 respectively display the same cross-section, and thus comprehensive diagnosis can be performed by observing these tomographic images comparatively.

Figure 10D:
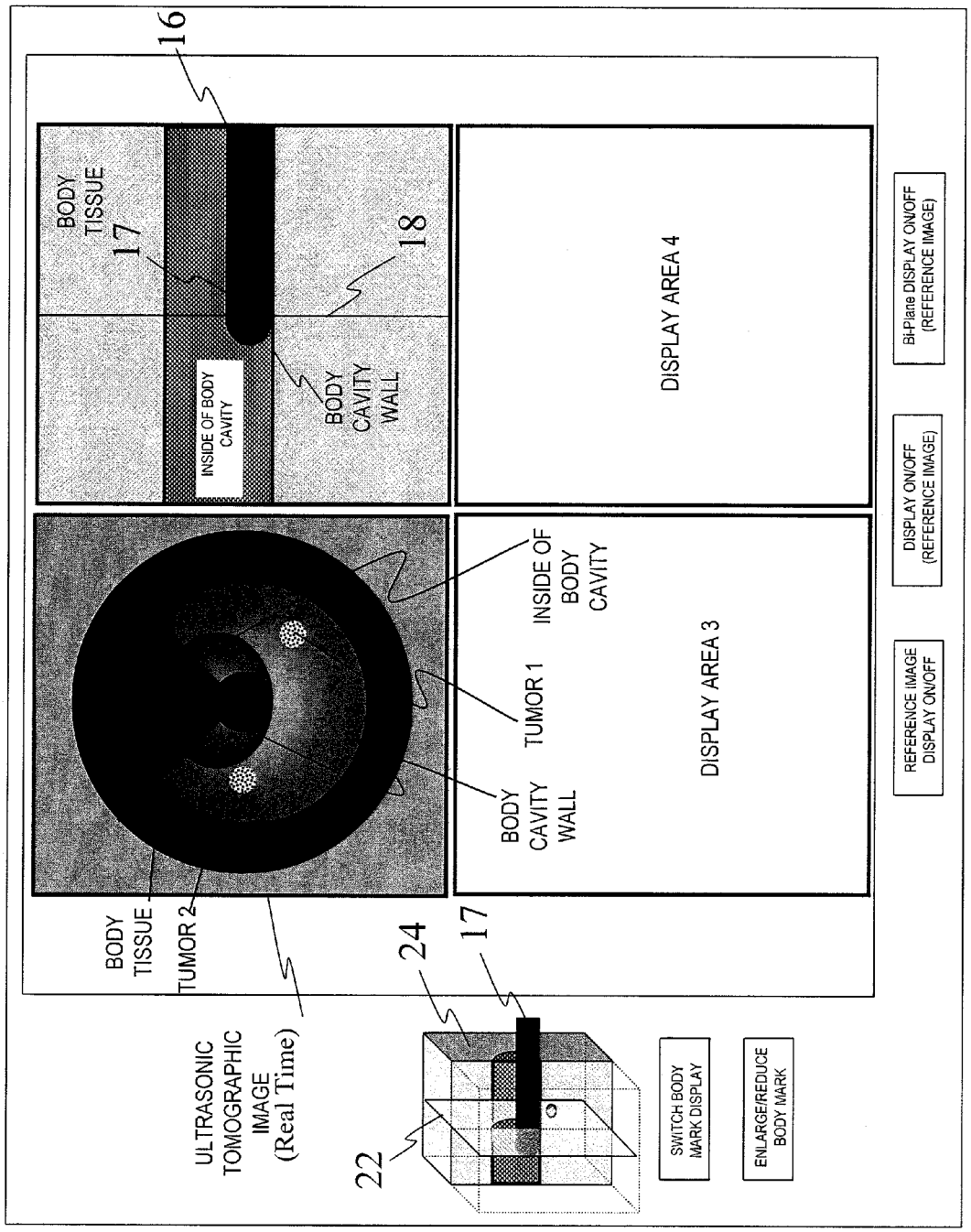
FIG. 10D is a diagram showing a display example of the monitor.

Furthermore, the present invention is not limited to the display styles of FIGS. 10A to 10C, but a display as shown in FIG. 10D may be performed. That is, the ultrasonic tomographic image, the travel-direction reference tomographic image 16 and the one half body mark 20 may be displayed.

Still furthermore, the display position relationship between the ultrasonic tomographic image and the reference tomographic image is not limited to those of FIGS. 10A to 10D. That is, it maybe set so that the ultrasonic tomographic image and the reference tomographic image are displayed at any places of the display areas 1 to 4.

Figure 11:
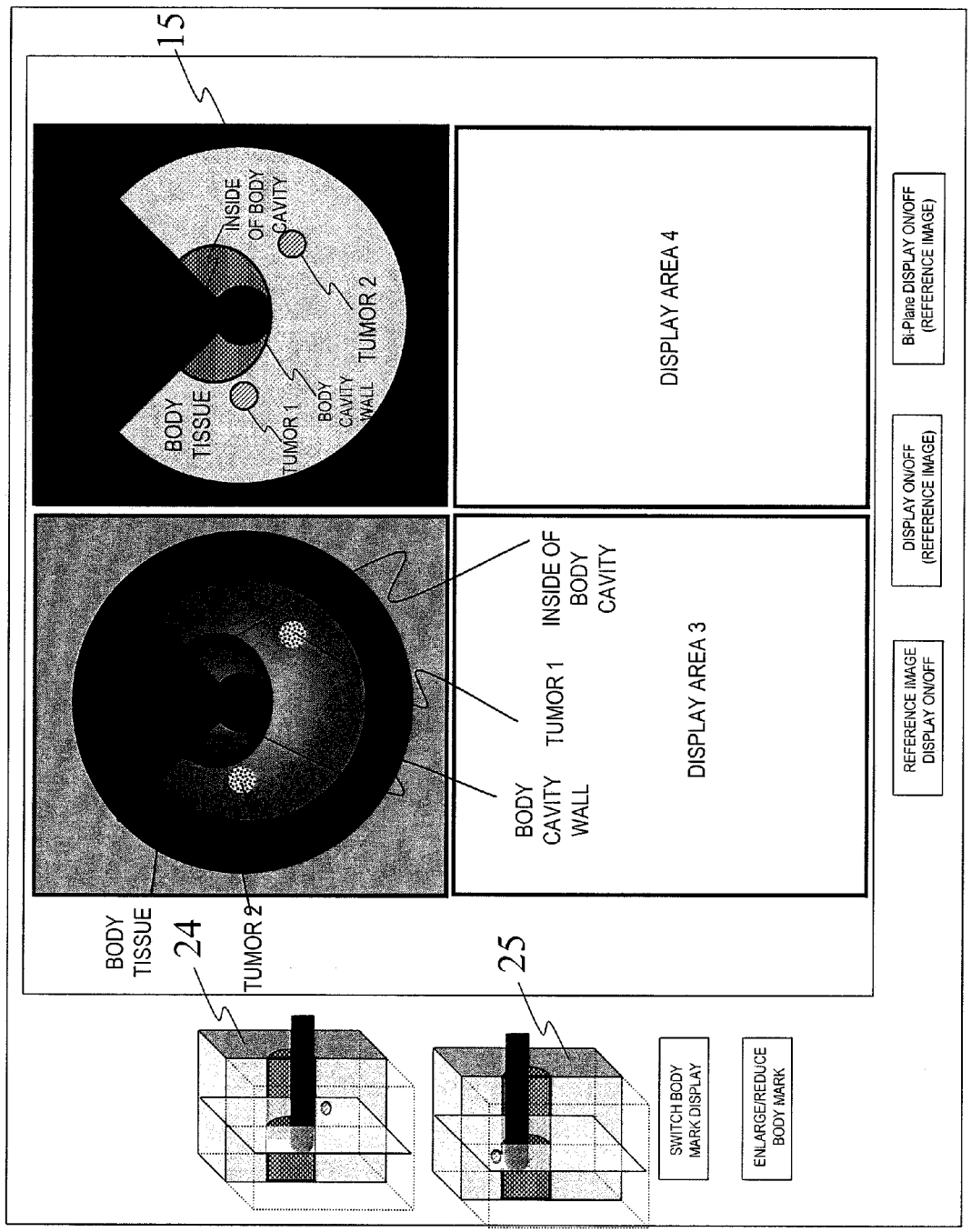
FIG. 11 is a diagram showing a display example of the monitor.

FIG. 11 shows a display screen when the body mark display switching button 30 is pushed in FIG. 10A. In this case, not only the one half body mark 24, but also the other half body mark 25 is displayed.

In this case, it is preferable that a second reference tomographic image having the same tomographic plane as an ultrasonic tomographic image is generated from reference three-dimensional volume data of the storage unit on the basis of an output of the position detector by using the image generating unit, and the ultrasonic tomographic image, the first reference tomographic image and the second reference tomographic image are displayed.

According to this manner, the position in the examinee at which the ultrasonic tomographic image and the second reference tomographic image are picked up and the information of the tomographic plane viewed from an angle different from these images can be grasped while a diagnosis is made by comparing the ultrasonic tomographic image and the second reference tomographic image, for example, and thus the diagnosis performance can be further enhanced.

Furthermore, when the ultrasonic probe is a biplane ultrasonic probe which also performs ultrasonic scanning in a direction perpendicular to the radial direction, the ultrasonic tomographic image in the radial direction, the ultrasonic tomographic image in the direction perpendicular to the radial direction, the first reference tomographic image and the second reference tomographic image are displayed, whereby further multilateral information can be provided to an operator.

Still furthermore, according to an ultrasonic diagnostic apparatus of a different embodiment according to this invention to solve the foregoing problem, it is known in the conventional technique that acquisition based on an image pickup device, that is, a three-dimensional body mark is generated on the basis of reference three-dimensional volume data. However, according to this embodiment, the three-dimensional body mark is cut by a tomographic plane extending parallel so as to contain the travel direction of the ultrasonic probe, and information on this tomographic plane is provided. In addition, a scanning position mark representing the position of the ultrasonic scanning is superimposed on this information to generate the half body mark. By displaying the half body mark together with the ultrasonic tomographic image, the operator can grasp the position in the examinee at which the ultrasonic tomographic image is picked up. Furthermore, the half body mark contains useful information such as a tumor or the like which is desired to be observed from a view angle different from the ultrasonic tomographic image, for example. Therefore, by displaying this information, the diagnosis performance can be enhanced.

In this case, the image generating unit can generate the other half body mark paired with one three-dimensional body mark while the scanning position mark representing the ultrasonic scanning position is superimposed on the other three-dimensional body mark, and display the ultrasonic tomographic image, the one half body mark and the other half body mark. That is, two half body marks can be generated by cutting a three-dimensional body mark, and the cut planes thereof are displayed so that an operator can see them, whereby the operator can be provided with further multilateral information.

In this invention, the ultrasonic tomographic image, the first reference tomographic image and the half body mark may be displayed.

Furthermore, some preferable embodiments of the ultrasonic diagnostic apparatus, etc. according to this invention are described with reference to the drawings. However, the present invention is not limited to the above embodiments. It is obvious that persons skilled in the art can make various kinds of alterations or modifications in the scope of the technical idea disclosed in this application, and it is understood that they belong to the technical scope of this invention.

DESCRIPTION OF REFERENCE NUMERALS

1 ultrasonic diagnostic apparatus body, 2 ultrasonic endoscope, 4 position sensor, 5 source generating source, 6 medical image diagnostic device, 7 volume image data storage unit, 8 ultrasonic image generating unit, 10 reference image generating unit, 11 3D body mark generating unit, 12 image processor, 13 monitor, 14 scan plane acquiring unit, 15 same-cross-section reference tomographic image, 16 travel-direction reference tomographic image, 18 scanning position mark, 19 three-dimensional body mark, 20, 21, 24 one half body mark, 25 the other half body mark, 40 ultrasonic diagnostic apparatus

The invention claimed is:

1. An ultrasonic diagnostic apparatus, characterized by comprising:
   a storage unit that stores reference three-dimensional volume data of an examinee obtained by an image pickup device;
   an ultrasonic probe that is configured to be inserted in a body cavity of the examinee and can perform ultrasonic scanning in a radial direction;
   an ultrasonic image generating unit that generates an ultrasonic tomographic image on the basis of a reflection echo signal from the ultrasonic probe;
   a position detector that detects a position and a posture of the ultrasonic probe on the basis of a sensor attached to the ultrasonic probe;
   an image generating unit that generates a scanning position mark representing an ultrasonic scanning position on a tomographic plane parallel to a travel direction of the ultrasonic probe from the reference three-dimensional volume data of the storage unit on the basis of an output of the position detector; and
   a display unit that displays the ultrasonic tomographic image and the scanning position mark.

2. The ultrasonic diagnostic apparatus according to claim 1, wherein the image generating unit generates a tomographic image having a tomographic plane parallel to the travel direction of the ultrasonic probe from reference three-dimensional volume data of the storage unit on the basis of an output of the position detector, and superimposes a scanning position mark representing an ultrasonic scanning position on the tomographic image to generate a first reference tomographic image.

3. The ultrasonic diagnostic apparatus according to claim 2, wherein the image generating unit generates a second reference tomographic image having the same tomographic plane as the ultrasonic tomographic image from the reference three-dimensional volume data of the storage unit on the basis of an output of the position detector, and the display unit displays the ultrasonic tomographic image, the first reference tomographic image and the second reference tomographic image.

4. The ultrasonic diagnostic apparatus according to claim 2, wherein the ultrasonic probe is a biplane ultrasonic probe for performing ultrasonic scanning in a direction perpendicular to the radial direction, and the display unit displays an ultrasonic tomographic image in the radial direction, an ultrasonic tomographic image in the direction perpendicular to the radial direction, the first reference tomographic image and the second reference tomographic image.

5. The ultrasonic diagnostic apparatus according to claim 1, wherein the image generating unit generates a three-dimensional body mark on the basis of reference three-dimensional volume data of an examinee, cuts the three-dimensional body mark by a tomographic plane parallel to the travel direction of the ultrasonic probe on the basis of an output of the position detector, and superimposes a scanning position mark representing an ultrasonic scanning position on one cut three-dimensional body mark to generate one half body mark.

6. The ultrasonic diagnostic apparatus according to claim 5, wherein the image generating unit superimposes the scanning position mark representing the ultrasonic scanning position on the other three-dimensional body mark paired with the one three-dimensional body mark to generate the other half body mark, and the display unit displays the ultrasonic tomographic image, the one half body mark and the other half body mark.

7. The ultrasonic diagnostic apparatus according to claim 5, wherein the image generating unit generates the three-dimensional body mark on the basis of the reference three-dimensional volume data of the examinee, cuts the three-dimensional body mark by the tomographic plane parallel to the travel direction of the ultrasonic probe on the basis of the output of the position detector, and superimposes the scanning position mark representing the ultrasonic scanning position on the one cut three-dimensional body mark to generate the one half body mark, and the display unit displays the ultrasonic tomographic image, the first reference tomographic image and the one half body mark.

8. The ultrasonic diagnostic apparatus according to claim 7, wherein the image generating unit generates a second reference tomographic image having the same tomographic plane as the ultrasonic tomographic image from the reference three-dimensional volume data of the storage unit on the basis of the output of the position detector, and the display unit displays the ultrasonic tomographic image, the first reference tomographic image, the one half body mark and the second reference tomographic image.

9. The ultrasonic diagnostic apparatus according to claim 7, wherein the image generating unit superimposes the scanning position mark representing the ultrasonic scanning position on the other three-dimensional body mark paired with the one three-dimensional body mark to generate the other half body mark, and the display unit displays the ultrasonic tomographic image, the first reference tomographic image, the one half body mark and the other half body mark.

10. A method of displaying a probe operation guide for an ultrasonic diagnostic apparatus, characterized by comprising:
  a first step that stores reference three-dimensional volume data of an examinee obtained by an image pickup device by a storage unit;
  a second step that inserts an ultrasonic probe into a body cavity of the examinee to perform ultrasonic scanning in a radial direction and generates an ultrasonic tomographic image on the basis of a reflection echo signal from the ultrasonic probe by an ultrasonic image generating unit;
  a third step that detects a position and a posture of the ultrasonic probe on the basis of a sensor attached to the ultrasonic probe by a position detector;
  a fourth step that generates a scanning position mark representing an ultrasonic scanning position on a tomographic plane parallel to a travel direction of the ultrasonic probe from the reference three-dimensional volume data of the storage unit on the basis of an output of the position detector by an image generating unit; and
  a fifth step that displays the ultrasonic tomographic image and the scanning position mark by a display unit.

11. An ultrasonic diagnostic apparatus, characterized by comprising:
  a storage unit that stores reference three-dimensional volume data of an examinee obtained by an image pickup device;
  an ultrasonic probe that is configured to be inserted in a body cavity of the examinee and can perform ultrasonic scanning in a radial direction;
  an ultrasonic image generating unit that generates an ultrasonic tomographic image on the basis of a reflection echo signal from the ultrasonic probe;
  a position detector that detects a position and a posture of the ultrasonic probe on the basis of a sensor attached to the ultrasonic probe;
  an image generating unit that generates a parallel plane image of a body section parallel to a travel direction of the ultrasonic probe from the reference three-dimensional volume data of the storage unit, with the parallel plane image including a scanning position mark generated on a basis of an output of the position detector and representing an ultrasonic scanning position of the ultrasonic tomographic image on the body section which is parallel to the travel direction of the ultrasonic probe; and
  a display unit that separately displays the ultrasonic tomographic image and the body section including the scanning position mark.

* * * * *